United States Patent
Hwang et al.

(10) Patent No.: US 9,943,549 B2
(45) Date of Patent: Apr. 17, 2018

(54) ISOLATION OF HUMAN NEURAL STEM CELLS FROM AMNIOTIC FLUID OF PATIENTS WITH NEURAL TUBE DEFECTS

(71) Applicant: FOOD INDUSTRY RESEARCH AND DEVELOPMENT INSTITUTE, Hsinchu (TW)

(72) Inventors: Shiaw-Min Hwang, Hsinchu (TW); Yu-Jen Chang, Hsinchu (TW); Lee-Feng Hsu, Hsinchu (TW)

(73) Assignee: FOOD INDUSTRY RESEARCH AND DEVELOPMENT INSTITUTE, Hsinchu (TW)

( * ) Notice: Subject to any disclaimer, the term of this patent is extended or adjusted under 35 U.S.C. 154(b) by 48 days.

(21) Appl. No.: 14/660,554

(22) Filed: Mar. 17, 2015

(65) Prior Publication Data
US 2016/0271182 A1 Sep. 22, 2016

(51) Int. Cl.
| | |
|---|---|
| C12N 5/073 | (2010.01) |
| A61K 35/30 | (2015.01) |
| C12N 5/0797 | (2010.01) |
| G01N 33/50 | (2006.01) |

(52) U.S. Cl.
CPC ............ *A61K 35/30* (2013.01); *C12N 5/0623* (2013.01); *G01N 33/5014* (2013.01); *G01N 33/5058* (2013.01)

(58) Field of Classification Search
None
See application file for complete search history.

(56) References Cited

U.S. PATENT DOCUMENTS

| | | |
|---|---|---|
| 6,294,346 B1 | 9/2001 | Weiss et al. |
| 2015/0025008 A1* | 1/2015 | Mayanil .............. A61K 31/4418 514/8.3 |

FOREIGN PATENT DOCUMENTS

| | | |
|---|---|---|
| CN | 102206611 | 10/2011 |
| WO | 2014/127289 | 8/2014 |

OTHER PUBLICATIONS

Tsurubuchi et al., J Neurosurg Pediatrics, 12:380-389, Oct. 2013.*
Mosquera et al., J Med Genet, 36:494-496, 1999.*
Yan et al., Neurochem Res, 38:1022-1033, 2013.*
Chen et al., Stem Cells, 25:1995-2005, 2007.*
Henderson et al., Stem Cells, 20:329-337, 2002.*
Search Report dated Jan. 19, 2016 in corresponding Taiwan patent application and English translation thereof, 7 pages total.
Turner et al., "The amniotic fluid as a source of neural stem cells in the setting of experimental neural tube defects," Stem Cells and Development, 2013, vol. 22, No. 4, pp. 548-553.
Tan et al., "Derivation of embryonic stem cell line from frozen human embryos and neural differentiation," Neuroreport, 2008, vol. 19, No. 15, pp. 1451-1455.
Okano H. Neural stem cells: progression of basic research and perspective for clinical application. The Keio journal of medicine. 2002;51:115-128.
Reynolds BA, Weiss S. Generation of neurons and astrocytes from isolated cells of the adult mammalian central nervous system. Science. 1992;255:1707-1710.
Kordower JH, Freeman TB, Snow BJ et al. Neuropathological evidence of graft survival and striatal reinnervation after the transplantation of fetal mesencephalic tissue in a patient with Parkinson's disease. The New England journal of medicine. 1995;332:1118-1124.
Hwang DH, Lee HJ, Park IH et al. Intrathecal transplantation of human neural stem cells overexpressing VEGF provide behavioral improvement, disease onset delay and survival extension in transgenic ALS mice. Gene therapy. 2009;16:1234-1244.
Andres RH, Horie N, Slikker W et al. Human neural stem cells enhance structural plasticity and axonal transport in the ischaemic brain. Brain: a journal of neurology. 2011;134:1777-1789.
Abematsu M, Tsujimura K, Yamano M et al. Neurons derived from transplanted neural stem cells restore disrupted neuronal circuitry in a mouse model of spinal cord injury. The Journal of clinical investigation. 2010;120:3255-3266.
Gonzalez-Perez O. Neural stem cells in the adult human brain. Biological and biomedical reports. 2012;2:59-69.
Schwartz PH, Bryant PJ, Fuja Tj et al. Isolation and characterization of neural progenitor cells from post-mortem human cortex. Journal of neuroscience research. 2003;74:838-851.
Vescovi AL, Parati EA, Gritti A et al. Isolation and cloning of multipotential stem cells from the embryonic human CNS and establishment of transplantable human neural stem cell lines by epigenetic stimulation. Experimental neurology. 1999;156:71-83.
Earl CD, Reum T, Xie JX et al. Foetal nigral cell suspension grafts influence dopamine release in the non-grafted side in the 6-hydroxydopamine rat model of Parkinson's disease: in vivo voltammetric data. Experimental brain research. 1996;109:179-184.
Ryder EF, Snyder EY, Cepko CL. Establishment and characterization of multipotent neural cell lines using retrovirus vector-mediated oncogene transfer. Journal of neurobiology. 1990;21:356-375.
De Filippis L, Ferrari D, Rota Nodari L et al. Immortalization of human neural stem cells with the c-myc mutant T58A. PloS one. 2008;3:e3310.
Zhang SC, Wernig M, Duncan ID et al. In vitro differentiation of transplantable neural precursors from human embryonic stem cells. Nature biotechnology. 2001;19:1129-1133.
Reubinoff BE, Itsykson P, Turetsky T et al. Neural progenitors from human embryonic stem cells. Nature biotechnology. 2001;19:1134-1140.
Chambers SM, Fasano CA, Papapetrou EP et al. Highly efficient neural conversion of human ES and iPS cells by dual inhibition of SMAD signaling. Nature biotechnology. 2009;27:275-280.

(Continued)

*Primary Examiner* — Kimberly Ballard
*Assistant Examiner* — Stacey N MacFarlane
(74) *Attorney, Agent, or Firm* — Hamre, Schumann, Mueller & Larson, P.C.

(57) ABSTRACT

The present invention provides a method for isolating human neural stem cells from amniotic fluid of a patient whose fetus has been diagnosed to have a neural tube defect. Use of the isolated human neural stem cells in the treatment of neurological disorders is also provided.

4 Claims, 14 Drawing Sheets

(56) References Cited

OTHER PUBLICATIONS

Miura K, Okada Y, Aoi T et al. Variation in the safety of induced pluripotent stem cell lines. Nature biotechnology. 2009;27:743-745.
Botto LD, Moore CA, Khoury MJ et al. Neural-tube defects. The New England journal of medicine. 1999;341:1509-1519.
Copp AJ, Greene ND. Genetics and development of neural tube defects. The Journal of pathology. 2010;220:217-230.
Copp AJ Stanier P, Greene ND. Neural tube defects: recent advances, unsolved questions, and controversies. Lancet neurology. 2013;12:799-810.
Yamaguchi Y, Miura M. How to form and close the brain: insight into the mechanism of cranial neural tube closure in mammals. Cellular and molecular life sciences: CMLS. 2013;70:3171-3186.
Kennedy D, Chitayat D, Winsor EJ et al. Prenatally diagnosed neural tube defects: ultrasound, chromosome, and autopsy or postnatal findings in 212 cases. American journal of medical genetics. 1998;77:317-321.
Wald N, Cuckle H, Nanchahal K. Amniotic fluid acetylcholinesterase measurement in the prenatal diagnosis of open neural tube defects. Second report of the Collaborative Acetylcholinesterase Study. Prenatal diagnosis. 1989;9:813-829.
Tsai MS, Lee JL, Chang YJ et al. Isolation of human multipotent mesenchymal stem cells from second-trimester amniotic fluid using a novel two-stage culture protocol. Hum Reprod. 2004;19:1450-1456.
De Coppi P, Bartsch G, Jr., Siddiqui MM et al. Isolation of amniotic stem cell lines with potential for therapy. Nature biotechnology. 2007;25:100-106.
Prusa AR, Marton E, Rosner M et al. Neurogenic cells in human amniotic fluid. American journal of obstetrics and gynecology. 2004;191:309-314.
Turner CG, Klein JD, Wang J et al. The amniotic fluid as a source of neural stem cells in the setting of experimental neural tube defects. Stem cells and development. 2013;22:548-553.
Swistowski A, Peng J, Liu Q et al. Efficient generation of functional dopaminergic neurons from human induced pluripotent stem cells under defined conditions. Stem Cells. 2010;28:1893-1904.
Longa EZ, Weinstein PR, Carlson S et al. Reversible middle cerebral artery occlusion without craniectomy in rats. Stroke; a journal of cerebral circulation. 1989;20:84-91.
McLaughlin D, Tsirimonaki E, Vallianatos G et al. Stable expression of a neuronal dopaminergic progenitor phenotype in cell lines derived from human amniotic fluid cells. Journal of neuroscience research. 2006;83:1190-1200.
Pennington EC, Gray FL, Ahmed A et al. Targeted quantitative amniotic cell profiling: a potential diagnostic tool in the prenatal management of neural tube defects. Journal of pediatric surgery. 2013;48:1205-1210.

McComb JG. Spinal and cranial neural tube defects. Seminars in pediatric neurology. 1997;4:156-166.
Emery AE, Brock DJ, Burt D et al. Amniotic fluid composition in malformations of the fetal central nervous system. The Journal of obstetrics and gynaecology of the British Commonwealth. 1974;81:512-516.
Reynolds BA, Rietze RL. Neural stem cells and neurospheres—reevaluating the relationship. Nature methods. 2005;2:333-336.
Ostenfeld T, Caldwell MA, Prowse KR et al. Human neural precursor cells express low levels of telomerase in vitro and show diminishing cell proliferation with extensive axonal outgrowth following transplantation. Experimental neurology. 2000;164:215-226.
De Filippis L, Lamorte G, Snyder EY et al. A novel, immortal, and multipotent human neural stem cell line generating functional neurons and oligodendrocytes. Stem Cells. 2007;25:2312-2321.
Tropepe V, Sibilia M, Ciruna BG et al. Distinct neural stem cells proliferate in response to EGF and FGF in the developing mouse telencephalon. Developmental biology. 1999;208:166-188.
Morshead CM, van der Kooy D. Disguising adult neural stem cells. Current opinion in neurobiology. 2004;14:125-131.
Bauer HC, Tempfer H, Bernroider G et al. Neuronal stem cells in adults. Experimental gerontology. 2006;41:111-116.
Capela A, Temple S. LeX/ssea-1 is expressed by adult mouse CNS stem cells, identifying them as nonependymal. Neuron. 2002;35:865-875.
Sun Y, Kong W, Falk A et al. CD133 (Prominin) negative human neural stem cells are clonogenic and tripotent. PloS one. 2009;4:e5498.
Tsai MS, Hwang SM, Tsai YL et al. Clonal amniotic fluid-derived stem cells express characteristics of both mesenchymal and neural stem cells. Biology of reproduction. 2006;74:545-551.
Zhang SC. Defining glial cells during CNS development. Nature reviews Neuroscience. 2001;2:840-843.
Zhang P, Li J, Liu Y et al. Human neural stem cell transplantation attenuates apoptosis and improves neurological functions after cerebral ischemia in rats. Acta anaesthesiologica Scandinavica. 2009;53:1184-1191.
Chen B, Gao XQ, Yang CX et al. Neuroprotective effect of grafting GDNF gene-modified neural stem cells on cerebral ischemia in rats. Brain research. 2009;1284:1-11.
Bliss T, Guzman R, Daadi M et al. Cell transplantation therapy for stroke. Stroke; a journal of cerebral circulation. 2007;38:817-826.
Hosper NA, Bank RA, van den Berg PP. Human amniotic fluid-derived mesenchymal cells from fetuses with a neural tube defect do not deposit collagen type I protein after TGF-beta1 stimulation in vitro. Stem cells and development. 2014;23:555-562.

* cited by examiner

ISOLATION OF HUMAN NEURAL STEM CELLS FROM AMNIOTIC FLUID OF PATIENTS WITH NEURAL TUBE DEFECTS

FIELD OF THE APPLICATION

The present application relates to human neural stem cells. More specifically, the present invention provides a method for isolating human neural stem cells from amniotic fluid of a patient whose fetus has been diagnosed to have a neural tube defect, and the uses of the isolated human neural stem cells.

BACKGROUND

Neural stem cells (NSCs) found in the central nervous system (CNS) have the capacity both to self-renew and to differentiate into each of the major cell types in brain. Ever since they were first described in mouse brain, NSCs have been the subject of intensive investigation because of their potential therapeutic use in treating neurodegenerative disorders [1, 2]. Specifically, transplanting NSCs may induce cellular repair and recovery of function after CNS injury or disease [3-6]. Previous studies have demonstrated that NSCs grafted into the CNS not only form new neurons but also express protective and trophic factors that are released into the damaged area.

Previously identified sources of NSCs in the adult mammalian CNS include the subgranular zone of the hippocampus and the subventricular zone of the ventral forebrain [7]. Human NSCs are typically obtained from aborted fetuses, post-mortem brains or surgical specimens [7-9]. However, the variability in donor age, storage, viability and potential contamination of these samples make it difficult to use them in therapeutic applications [10]. Other barriers include limited availability, technical difficulty in harvesting, and ethical concerns. Finally, the slow kinetics of human NSCs growth in primary cultures imposes a severe limitation on the ability to obtain enough quality cells for clinical applications. Recently, some immortalized neural stem/progenitor cell lines have been established [11, 12], which possess a relatively higher capacity for proliferation than typical NSCs while still retaining the ability to differentiate into different neural cell types. However, the use of oncogenic genes and viral infection in establishing these lines raises vital concerns over risk in medical-oriented applications. Other groups have established lines from pluripotent sources of stem cells such as embryonic stem cells or induced pluripotent stem cells [13-15]. While these methods do introduce a new source of NSCs, the possibility remains that undifferentiated cells will persist in these populations and could consequently form teratomas [16]. Therefore, the ability to use pluripotent stem cell-derived NSCs for therapeutic applications is limited by ethical issues, safety concerns, and poor efficiency.

Neural tube defects (NTDs) are the most common defects when a neural tube develops abnormally, and they affect approximately 1 in 1000 pregnancies [17]. The neural tube is formed during embryonic development and eventually gives rise to the entire CNS. When the neural tube does not close completely on either end, an NTD occurs. In humans, the most common NTDs are anencephaly and myelomeningocele. The former results from a failed closure of the rostral end of the neural tube and is characterized by a total or partial absence of the cranial vault and cerebral hemisphere, while the latter is a defective closure of the caudal neural tube and the vertebral column [18-20]. Anencephaly results in incomplete formation of the brain and skull and is therefore lethal. Most individuals with myelomeningocele have a multiple system handicap and a limited lifespan. Either ultrasound technology or measurement of maternal serum alpha-fetal protein levels can be used to detect an NTD in utero [21]. Follow-up testing typically measures the levels of alpha-fetal protein and acetylcholinesterase in the amniotic fluid to confirm that an NTD is present [22].

Amniotic fluid (AF) is known to contain multiple cell types that are derived from the developing fetus, and previous studies have demonstrated that multipotent stem cells can be isolated from this substance via amniocentesis. These AF-derived stem cells (AFSCs) express some pluripotent markers and can differentiate into cells of mesenchymal or neural lineages under inductive conditions [23-25]. Although AFSCs exhibit neural potentiality both in vivo and in vitro, they lack some typical properties of NSCs, such as proper growth, morphology and the potential to form neurospheres. To date, no group has been able to isolate NSCs directly from normal amniotic fluid samples of any species. Recently, one group reported that NSCs could be established from the amniotic fluid of pregnant rats in which the fetus had an NTD [26].

Human neural stem cells (NSCs) are a particularly valuable tool for the study of both nerve system development and the function of adult neurogenesis. NSCs also have great therapeutic potential in treating neurodegenerative disorders. However, current sources of human NSCs are limited for technical reasons such as the difficulty in isolating them and the time needed to expand the population.

Therefore, there is still a need to develop a method to obtain human NSCs which can be expanded for long periods without losing their stem cell-specific properties.

SUMMARY OF THE INVENTION

One aspect of the invention relates to a method for obtaining isolated human neural stem cells from amniotic fluid obtained from a pregnant human subject whose fetus has been diagnosed to have a neural tube defect, wherein the isolated human neural stem cells express Nestin, Sox2, Musashi-1 and ATP-binding cassette G2 (ABCG2) markers but do not express SSEA-3, SSEA-4, TRA-1-60 and TRA-1-81.

Another aspect of the invention relates to isolated human neural stem cells obtained from the method of the present invention.

Another aspect of the invention relates to a pharmaceutical composition comprising the isolated human neural stem cells obtained from the method of the present invention and a pharmaceutically acceptable carrier.

Another aspect of the invention relates to a method for treating a neurological condition in a mammal in need thereof, comprising administering the pharmaceutical composition of the present invention to the mammal.

Another aspect of the invention relates to a method for screening drug candidates, wherein the method comprises the steps of contacting the isolated human neural stem cells obtained from the method of the present invention with a drug candidate; and determining one or more cell conditions of the cells; if the determined one or more cell conditions are better than the same condition(s) of the cells without contacting the drug candidate, it represents that the drug candidate has potential in the treatment of neurological conditions.

Another aspect of the invention relates a method for testing the cytotoxicity of a drug candidate, wherein the method comprises the steps of contacting the isolated human neural stem cells obtained from the method of the present invention with the drug candidate; and determining one or more cell conditions of the cells; if the determined one or more cell conditions are poorer than the same condition(s) of the cells without contacting the drug candidate, it represents that the drug candidate may have cytotoxicity.

DETAILED DESCRIPTION

Figure 1A:
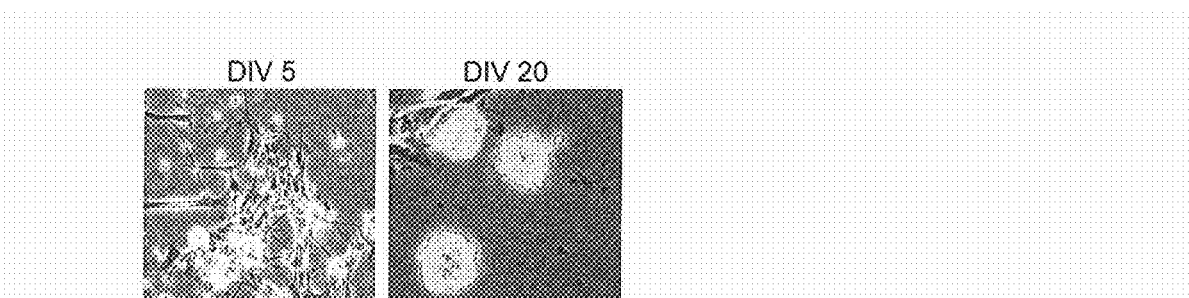
FIG. 1A shows the culture properties of AF-NSCs. After initial seeding of the amniotic fluid cells in NeuroCult™ NS-A proliferation medium, neural-like cells began to attach to the culture plate (left hand panel). These cells then proliferated and rounded up to form suspended primary neurospheres (right hand panel). Abbreviations: DIV: days in vitro.

The present invention can be understood more readily by reference to the following detailed description of various embodiments of the invention, the examples, and the tables with their relevant descriptions. Unless otherwise defined, all terms (including technical and scientific terms) used herein have the same meaning as commonly understood by one of ordinary skill in the art to which this invention belongs. It will be further understood that terms such as those defined in commonly used dictionaries should be interpreted consistently with their meaning in the context of the relevant art and will not be interpreted in an idealized or overly formal sense unless expressly so defined herein. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±20%, preferably ±10%, and even more preferable ±5%.

The present invention discloses isolated and propagated human NSCs which are obtained from amniotic fluid that is taken from a patient whose fetus has been diagnosed to have a neural tube defect (NTD). These amniotic fluid-derived NSCs (AF-NSCs) form neurospheres and undergo long-term expansion in vitro. Additionally, they express NSCs-specific markers including Nestin, Sox2, Musashi-1 and ATP-binding cassette G2 (ABCG2) and also exhibit telomerase activity. After they are induced to differentiate in vitro, AF-NSCs display typical morphological patterns and express specific markers that are consistent with neurons, astrocytes, oligodendrocytes and dopaminergic neurons. Furthermore, AF-NSCs can be grafted into an animal to treat neurological disorders.

Therefore, the present invention provides a method for obtaining isolated human neural stem cells, which comprises:

(a) collecting the cells from amniotic fluid obtained from a pregnant human subject whose fetus has been diagnosed to have a neural tube defect (NTD);

(b) incubating the cells with a culture medium; and (c) isolating the human neural stem cells from the culture medium, wherein the isolated human neural stem cells express Nestin, Sox2, Musashi-1 and ATP-binding cassette G2 (ABCG2) markers and exhibit telomerase activity but do not express SSEA-3, SSEA-4, TRA-1-60 and TRA-1-81.

A neural stem cell is an undifferentiated neural cell that can be induced to proliferate. The neural stem cell is capable of self-maintenance, meaning that with each cell division, one daughter cell also be a stem cell. Therefore, the phrase "neural stem cell" as used herein shall be understood to include, whenever appropriate, true stem cells as well as neural progenitor cells.

According to the invention, the neural tube defects (NTDs) include, but are not limited to, anencephaly and myelomeningocele. More specifically, the NTD is anencephaly.

In step (a) of the invention, the cells may be collected by any method known in the art. For example, centrifugation and/or filtration of the amniotic fluid can be used.

According to the invention, the culture medium represents any medium that allows the neural stem cells to proliferate. The culture medium may be, but is not limited to, NeuroCult™ NS-A Proliferation medium (StemCell Technologies, Vancouver, BC, Canada), Stemline™ Neural Stem Cell Expansion Medium (Sigma) (20 ng/ml epidermal growth factor (Sigma) and 10 ng/ml leukaemia inhibitory factor (Chemicon) are additionally added), NS-A medium (Euroclone) (1×N2 and 10 ng/ml each of EGF (PeproTech) and bFGF are additionally added), NS-A basal serum-free medium (Euroclone) (20 human recombinant EGF ng/ml, 10 ng/ml human recombinant FGF2, 2 mM L-glutamine, 0.6% glucose, 9.6 µg/ml putrescine, 6.3 ng/ml progesterone, 5.2 ng/ml sodium selenite, 0.025 mg/ml insulin, and 0.1 mg/ml trans-ferrin (sodium salt, grade II; Sigma; control medium) are additionally added), Dulbecco's minimal essential medium (DMEM)/F12 (1:1) (B27 supplementation (1:50), 2 mM glutamine, 50 units/ml penicillin 50 µg/ml streptomycin (Gibco), 20 ng/ml human recombinant EGF, and 20 ng/ml bFGF (R&D Systems) are additionally added), and Dulbecco's modified Eagle's medium (DMEM)/HAMS-F12 (3:1, Gibco) (penicillin G/streptomycin/amphotericin B (1% v/v; Gibco), B27 supplement (2% v/v, Gibco), epidermal growth factor (EGF, 20 ng/ml, Sigma), and fibroblast growth factor 2 (FGF-2, 20 ng/ml, R&D Systems) with heparin (5 mg/ml, Sigma) are additionally added).

The present invention also provides isolated human neural stem cells which have all of the same characteristics as those of the neural stem cells obtained from the method of the present invention. The cells of the invention are of use as a source of cells for cell therapy. For example, the cells can be transplanted to restore damaged neural circuitry and/or restore brain function.

In certain embodiments, the isolated cells are present within a pharmaceutical composition. Accordingly, the pharmaceutical composition comprising the neural stem cells further comprises a pharmaceutically acceptable carrier, such as one or more buffers (neural buffered saline or phosphate buffered saline), solutes that render the formulation isotonic, hypotonic or weakly hypertonic with the blood of a recipient, suspending agents, thickening agents and/or preservatives.

In some embodiments, the pharmaceutical composition is formulated in a unit dosage injectable form, such as a solution, suspension, or emulsion. Pharmaceutical compositions suitable for injection of cells typically are sterile aqueous solutions and dispersions. Carriers of injectable formulations can be a solvent or dispersing medium containing, for example, water, saline, phosphate buffered saline, polyol (e.g., glycerol, propylene glycol, liquid polyethylene glycol, and the like), and suitable mixtures thereof.

The skilled artisan can readily determine the amount of cells and optional additives, vehicles, and/or carrier in the pharmaceutical composition of the invention. Typically, any additives (in addition to the cells) are present in an amount of about 0.001 to about 50 wt % in solution, such as in phosphate buffered saline. The active ingredient is present in the order of micrograms to milligrams, such as about 0.0001 to about 5 wt %, preferably about 0.0001 to about 1 wt %, and most preferably about 0.0001 to about 0.05 wt %; or about 0.001 to about 20 wt %, preferably about 0.01 to about 10 wt %, and most preferably about 0.05 to about 5 wt %.

Neural stem cells can be used for transplantation into a heterologous, autologous, or xenogeneic host. The neural stem cell progeny can be administered to any animal with abnormal neurological or neurodegenerative symptoms obtained in any manner, including those obtained as a result of mechanical, chemical, or electrolytic lesions, as a result of ischemia or hypoxia of neural areas, or as a result of aging processes.

Therefore, the present invention also relates to a method for treating a neurological condition in a mammal in need thereof, which comprises administering the pharmaceutical composition of the present invention to the mammal.

The terms "treating" and "treatment" mean the slowing, interrupting, arresting or stopping of the progression of the disease or condition and do not necessarily require the complete elimination of all disease symptoms and signs. "Preventing" or "prevention" is intended to include the prophylaxis of the neurological disease, wherein "prophylaxis" is understood to be any degree of inhibition of the time of onset or severity of signs or symptoms of the disease or condition, including, but not limited to, the complete prevention of the disease or condition.

Neurological conditions that can be treated according to the present invention can be generally classified into three classes: those diseases with ischemic or hypoxic mechanisms; neurodegenerative diseases; and neurological and psychiatric diseases associated with neural cell death. Other neurological conditions that can be treated according to the present invention also include enhancing cognitive ability and the treatment of brain tumors, such as glioblastomas, astrocytomas, meningiomas, and neurinomas.

Diseases with ischemic or hypoxic mechanisms can be further subclassified into general diseases and cerebral ischemia. Examples of such general diseases involving ischemic or hypoxic mechanisms include myocardial infarction, cardiac insufficiency, cardiac failure, congestive heart failure, myocarditis, pericarditis, perimyocarditis, coronary heart disease (stenosis of coronary arteries), angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, and pulmonary edema. Examples of cerebral ischemia disease include stroke (as well as hemorrhagic stroke), cerebral microangiopathy (small vessel disease), intrapartal cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, and diabetic retinopathy.

Examples of neurodegenerative diseases include amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Sträussler-Schanker disease, Creutzfeld-Jakob-disease, Machado-Joseph disease, Friedreich ataxia, non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

Examples of neurological and psychiatric diseases associated with neural cell death include septic shock, intracerebral bleeding, subarachnoidal hemorrhage, multiinfarct dementia, inflammatory diseases (such as vasculitis, multiple sclerosis, and Guillain-Barre-syndrome), neurotrauma (such as spinal cord trauma, and brain trauma), peripheral neuropathies, polyneuropathies, epilepsies, schizophrenia, depression, metabolic encephalopathies, and infections of the central nervous system (viral, bacterial, fungal).

Since the human neural stem cells isolated by the present invention can form neurospheres, undergo long-term expansion and differentiate into astrocytes, oligodendrocytes and dopamineric neurons in vitro, the isolated human neural stem cells are suitable for drug discovery or neurotoxicity test.

Therefore, the present invention further relates to an in vitro method for screening drug candidates, which comprises contacting the isolated human neural stem cells with a drug candidate; and determining one or more cell conditions of the cells; if the determined one or more cell conditions are better than the same condition(s) of the cells without contacting the drug candidate, it represents that the drug candidate has potential in the treatment of neurological conditions.

In addition, a cytotoxic testing method may be included in the present invention. The method is conducted in vitro and comprises the steps of contacting the isolated human neural stem cells with a drug candidate; and determining one or more cell conditions of the cells; if the determined one or more cell conditions are poorer than the same condition(s) of the cells without contacting the drug candidate, it represents that the drug candidate has cytotoxicity.

According to the invention, the isolated human neural stem cells may be provided in the form of a neurosphere culture or a monolayer culture; and the drug candidate to be tested may be an organic or inorganic chemical, a peptide, a polypeptide or a protein; and the cell condition determined may include, but is not limited to, neurosphere formation, apoptosis, proliferation, differentiation, migration, or any combination thereof.

The cell conditions may be determined by any method known in the art for observing the changes of phenotype and/or genotype of cells. For example, neurosphere formation, apoptosis, proliferation, differentiation and migration may be observed by using phase-contrast microscopy. Colorimetric and immunofluorescent-based assay may also be used. Furthermore, technologies such as gene expression, electrical activity measurements and metabonomics can be used as tools. For example, measurement of the level of mRNA of a cell marker which represents a specific stage of cell development and maturation can be used.

According to the invention, the term "better" means that the level of cell condition (e.g., cell count, neurosphere diameter or metabolic activity measured over time) of the drug candidate-contacted human neural stem cells is "higher" than that from the non-drug candidate-contacted human neural stem cell; and the term "poorer" means that the level of cell condition (e.g., cell count, neurosphere diameter or metabolic activity measured over time) of the drug candidate-contacted human neural stem cells is "lower" than that from the non-drug candidate-contacted human neural stem cell. In one embodiment of the present invention, the term "better" represents at least 0.5-fold higher, and preferably at least 1-fold higher; and the term "poorer" represents 0.5-fold lower, and preferably at least 1-fold lower.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Materials and Methods
Sample Collection

The amniotic fluid samples used in this study were obtained from Cathay General Hospital in Taipei and Chang Gung Memorial Hospital in Taoyuan, Taiwan. Pregnant women aged 25 to 35 years underwent amniotic fluid sampling performed for diagnostic purposes between 16 and 20 weeks gestation. Fetuses were diagnosed with an NTD of anencephaly or without an NTD by ultrasound and screening of maternal serum. All procedures were approved by the Institutional Review Boards of Cathay General Hospital and Chang Gung Memorial Hospital, and all participants provided written informed consent to participate in this study.

Cultivation of AF-NSCs

Each amniotic fluid sample was centrifuged at 1,000 rpm for 5 min, and the cell pellet was resuspended in NeuroCult™ NS-A Proliferation medium (StemCell Technologies, Vancouver, BC, Canada) in a T25 flask at 37° C. in a 5% $CO_2$ humidified atmosphere. After 3-5 days, some attached neural-like cells could be observed from the NTD samples, and the suspended cells and debris were removed by changing the media. After adding fresh NeuroCult™ NS-A proliferation medium, the attached neural-like cells replicated and rounded-up to form primary neurohsperes. To maintain these cells, 1/5 volume of additional culture medium was added every 2-3 days. The initial mature neurospheres could be observed 3-4 weeks after plating. These cells were designated as human amniotic fluid derived neural stem cells (AF-NSCs).

When the neurospheres grew to 50-100 μm in diameter, these cells were passaged. First, the cells were centrifuged at 800 rpm for 5 min and treated with TrypLE (Life Technologies, Gaithersburg, Md., USA) at 37° C. for 3 min. After an additional centrifugation step to remove the TrypLE solution, the cells were resuspended in the NeuroCult NS-A proliferation medium, and a single cell suspension was obtained by pipetting carefully to avoid bubble formation. AF-NSCs were seeded at a density of $0.5\text{-}1\times10^4/cm^2$ and were maintained as described above. Neurospheres were passaged every 10-14 days, and the AF-NSCs could be expanded for more than 8 months in vitro. The neurospheres could also be cryopreserved for subsequent experiments.

To determine the optimal seeding density, the AF-NSCs were plated at densities from 1,000-20,000 cells/cm² in a T25 flask and cultured as previously described. After 10 days, the neurospheres were collected and trypsinized. Cell counts were performed with a hemocytometer, and the doubling time per passage was calculated. Each of the described experiments was performed in triplicate.

In cumulative cell number test, AF-NSCs were seeded at 5,000 cells/cm² in a T25 flask and cultured as previously described. The cells were passaged every 10-14 days, and cells counts were performed at each passage to calculate the fold increase in cells along with the total cell number.

Flow Cytometry

AF-NSCs were trypsinized and resuspended as single cells in phosphate buffered saline (PBS). For direct analysis, the cells were fixed with Cytofix™ (BD Biosciences, San Jose, Calif., USA) with or without permeabilization, and immunolabeled with the following anti-human antibodies: CD73-phycoerythrin (PE), CD105-Fluorescein isothiocyanate (FITC), CD117-PE, HLA-I-PE, HLA-DR-PE, Nanog-PE, Oct-4-FITC, Sox2-PE, ABCG2-PE (all from BD Biosciences), SSEA-1-PE, SSEA-3-FITC, SSEA-4-PE, TRA-1-60-PE, TRA-1-81-PE, Nestin-FITC (all from R&D Systems, Minneapolis, Minn., USA) or CD133-PE (Merck Millipore, Billerica, Mass., USA). For indirect analysis, the cells were fixed, permeabilized with Perm Buffer II (BD Biosciences), blocked, immunolabeled with Musashi-1 (R&D Systems) and stained with an Alexa Fluor 488 dye (Life technologies). All samples were processed using a FACSCantoII flow cytometer (BD Biosciences), and at least 30,000 events were captured per sample. The data acquisition and analysis were performed using FACSDiva 6.0 (BD Biosciences) and FCS Express V3.00 (De Novo Software, Thornhill, Canada).

Immunocytochemistry

The cells were fixed with 4% paraformaldehyde (Merck Millipore) and permeabilized with 0.1% Triton X-100 (Sigma-Aldrich, St Louis, Mo.). After being blocked with 10% specific normal serum in PBS for 30 min, the cells were incubated with the appropriate primary antibodies: Tuj-1 (Sigma), Nestin, Sox2, microtubule-associated protein 2 (MAP2), neural filament heavy chain (NFH), glial fibrillary acidic protein (GFAP), human neuron-specific nuclear protein (hNeuN), tyrosine hydroxylase (TH) (all from Merck Millipore), Musashi-1, O4, or aromatic L-amino acid decarboxylase (AADC) (all from R&D system) for 1 hr. After being washed twice, the cells were then incubated with an Alexa Fluor 488 or Alexa Fluor 546-conjugated secondary antibody (Life Technologies) for 1 hr at room temperature. The resulting immunoreactive cells were visualized under a confocal microscope (TCS-SPS-X AOBS, Leica, Solms, Germany) or a fluorescent microscope (Axio Observer.Z1, Carl Zeiss, Oberkochen, Germany).

Telomerase Activity Assay

Telomerase activity was measured by the telomeric repeat amplification protocol (TRAP) using a commercially available TRAPeze RT kit (Merck Millipore). The amplified TRAP reaction products were separated on a 12.5% polyacrylamide gel and visualized as TRAP ladder patterns.

Quantitative Polymerase Chain Reaction (qPCR)

Total RNA was extracted with the TRIzol Reagent (Invitrogen, Carlsbad, Calif., USA), and first strand cDNA was synthesized according to the manufacturer's protocol using M-MuLV Reverse Transcriptase (Thermo Scientific, San Jose, Calif., USA) and an oligo-dT primer. qPCR was performed with the SYBR Green PCR master mix (Thermo Scientific) using the ABI Prism 7700 Sequence Detection System (Applied Biosystems, Foster City, Calif.). The relative expression level of β-actin was used as an internal control to normalize gene expression in each sample. Relative quantification of marker genes was performed according to the ΔΔCt method. The primer pairs used in this study are listed in Table 2.

TABLE 2

Oligonucleotide primers used in this study.

| Primer | Sequence (5' to 3') | SEQ ID No. |
|---|---|---|
| Nestin | Forward: CCCTGACCACTCCAGTTTAG | 1 |
| | Reverse: CCTCTATGGCTGTTTCTTTCTC | 2 |
| Sox-2 | Forward: CCGGCACGGCCATTAAC | 3 |
| | Reverse: CTCCCATTTCCCTCGTTTTTC | 4 |
| Oct-4 | Forward: TGCAGGCCCGAAAGAGAAAG | 5 |
| | Reverse: GATCTGCTGCAGTGTGGGTTT | 6 |
| Nanog | Forward: TGCCTCACACGGAGACTGTCT | 7 |
| | Reverse: AGTGGGTTGTTTGCCTTTGG | 8 |
| hTERT | Forward: AGCTATGCCCGGACCTCCAT | 9 |
| | Reverse: GCCTGCAGCAGGAGGATCTT | 10 |
| Tuj-1 | Forward: AAGCCAGCAGTGTCTAAACCC | 11 |
| | Reverse: GGGAGGACGAGGCCATAAATAC | 12 |
| MAP2 | Forward: GTGACAAGGAGTTTCAAACAGGAA | 13 |
| | Reverse: CTGATGGATAACTCTGTGCGAGA | 14 |
| GFAP | Forward: GCGAGGAGAACCGGATCAC | 15 |
| | Reverse: TTCACCACGATGTTCCTCTTGA | 16 |

TABLE 2-continued

Oligonucleotide primers used in this study.

| Primer | Sequence (5' to 3') | SEQ ID No. |
|---|---|---|
| CNP | Forward: CCCAGGGAGAAGATGGACTTG | 17 |
|  | Reverse: CTTTAACACATCTTGTTGAGCGTACTC | 18 |
| MBP | Forward: AGGCAGAGCGTCCGACTATAAA | 19 |
|  | Reverse: GACTATCTCTTCCTCCCAGCTTAAAA | 20 |
| O2 | Forward: CGGCGTTCGGTATCAGA | 21 |
|  | Reverse: GAACGGCCACAGTTCTAAGAG | 22 |
| AADC | Forward: GGACCACAACATGCTGCTC | 23 |
|  | Reverse: CACTCCATTCAGAAGGTGCC | 24 |
| Lmx-1b | Forward: CCGAAAGGTCCGAGAGACACT | 25 |
|  | Reverse: AGCTTCTTCATCTTTGCTCTTTGG | 26 |
| Pax2 | Forward: CCTGACCCCTGGGCTTGAT | 27 |
|  | Reverse: GTATGTCTGTGTGCCTGACACGTT | 28 |
| Nurr-1 | Forward: GGCGAACCCTGACTATCAAATG | 29 |
|  | Reverse: GCCCCGGATGATCTCCAT | 30 |
| β-actin | Forward: TGTGGATCAGCAAGCAGGAGTA | 31 |
|  | Reverse: CAAGAAAGGGTGTAACGCAACTAAG | 32 |

AF-NSC Differentiation

The AF-NSCs-derived neurospheres (passage #10-12) were trypsinized and seeded in NeuroCult™ NS-A proliferation medium at a density of $5 \times 10^4$ cells/cm$^2$ on 100 ng/ml poly-L-lysine-(Sigma-Aldrich) and 10 ng/ml laminin-(Sigma-Aldrich) coated culture dishes. Upon cell attachment to the bottom of the dishes, neural differentiation was induced by the addition of NeuroCult™ NS-A differentiation medium (StemCell Technologies) according to the manufacture's protocol. After induction, the differentiated cells were fixed with 4% paraformaldehyde for immunocytochemistry or collected for mRNA extraction and subsequent qPCR. To direct the differentiation of specific cell types, AF-NSCs were seeded on plates coated with 100 ng/ml poly-L-lysine at a density of $5 \times 10^4$ cells/cm$^2$ in the presence of NS-A proliferation medium. After attachment, the medium could be changed to a specific induction medium that would produce astrocytes, oligodendrocytes and dopamineric neurons were according to the previously published protocols [27].

Focal Ischemia and AF-NSCs Transplantation

All the Sprague-Dawley rats (8 wks old, 250-300 g) were obtained from Lasco (Ilan, Taiwan) and housed in an animal facility at National Chung Hsing University. All experimental procedures were devised with the welfare of the animal in mind and were approved by the Institutional Animal Care and Use Committee of National Chung Hsing University. The rats (n=12) were subjected to a 1.5 hr long suture occlusion of the middle cerebral artery (MCAO) in the right hemisphere [28]. On the first post-operative day, $1 \times 10^6$ AF-NSCs (passage #10-12, 10 µL, 1 µL/min) were transplanted into the damaged striatum at the location of AP: −0.4 R: 3.4 DV:5 (n=6). The animals were sacrificed 4 weeks after the operation, and their brains were fixed with 4% paraformaldehyde by transcardial perfusion.

Behavioral Assays

MCAO rats underwent both rotarod and grip strength assays. All rats performed similarly on both pieces of equipment after one week of training. For the rotarod test, sham-operated rats could remain on the cylinder when it was accelerated from 4 to 40 rpm within 300 s. To test their grip strength, the rats grasped the pull bar with their forepaws, and their grip strength was quantified by an electronic sensor that was connected to the bar. The results of three trials for each rat were recorded.

TTC Staining and Immunohistochemistry

MCAO rats brains were sectioned coronally into 6 slices, which were then immersed with 2% 2,3,5-triphenyltetrazolium chloride (TTC) for 30 minutes at 37° C. followed by formalin fixation. Infarcted areas were pale, while normal brain tissue was stained red. For comparison with the area of healthy hemisphere, the residual portion of stroke hemisphere in which the pale infracted, the hollow liquidation and the normal tissue region had diminished was assigned as the atrophy area. The infarcted and atrophied areas were estimated with a computer image analysis system (Image-Pro Plus, Media Cybernetics, Carlsbad, Calif., USA), and the extent of tissue damage was calculated as a percentage of the total area of the contralateral healthy hemisphere.

For the immunohistochemical analysis, the brains were dehydrated with a sucrose gradient, embedded with OCT (Sakura Fine Technical, Tokyo, Japan), frozen at −70° C., and cryosectioned at a thickness of 40 µm. For immunostaining, the sections were rinsed in PBS containing 0.1% Tween-20 (PBST), permeabilized with 0.1% Triton X-100, and blocked with 10% specific normal serum in PBS for 30 min prior to overnight incubation with the primary antibodies, including the human Nuclei (Merck Millipore) and Nestin (Merck Millipore). Next, the sections were washed twice with PBST and incubated with the appropriate rhodamine- or FITC-conjugated secondary antibody (Thermo Scientific) for 1 hr at room temperature. Finally, a fluorescent microscope was used to visualize the distribution of labeled cells.

Statistical Analysis

All results in the examples are presented as mean±standard deviation (SD). Significant differences between the two mean values were compared using the Student's t-test. One-way ANOVA with Scheffe's post hoc test was used to assess significant differences if more than two groups were compared. The results were considered statistically significant when $p<0.05$.

Example 1. Isolation of NSCs from Amniotic Fluid

Figure 1B:
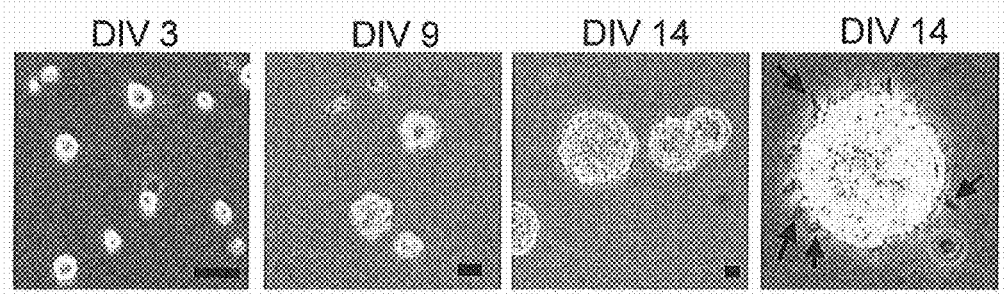
FIG. 1B shows the culture properties of AF-NSCs. While the neurospheres were dissociated into a single cell suspension for plating, afterwards, they continued to divide and re-formed into neurospheres. Mature AF-NSC-derived neurospheres contained a typical micro-spike structure over the outer surface (right, black arrows). Scale bar: 10 µm. Abbreviations: DIV: days in vitro.
Figure 6:
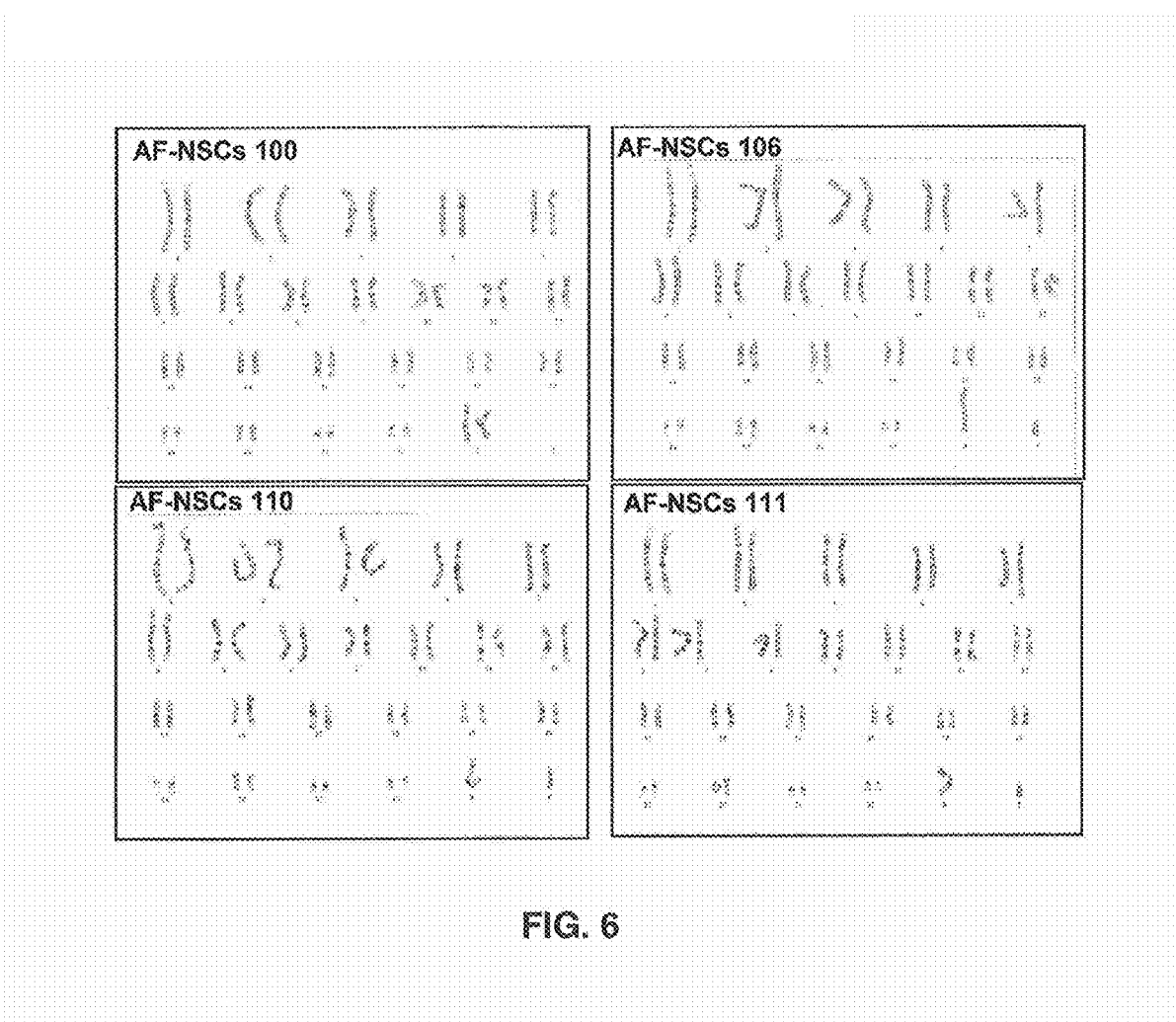
FIG. 6 shows the karyotypes of the 4 AF-NSC lines that were established in this study. All 4 of the AF-NSCs lines possess normal karyotypes, including one 46XX and three 46XY.

To isolate NSCs from amniotic fluid, normal (n=7) and NTD (anencephaly n=6, non-anencephaly n=6)-derived amniotic fluid specimens were collected by amniocentesis. When the cells isolated from these samples were cultured in NeuroCult™ NS-A proliferation medium, only a subset of the anencephaly samples produced some slightly attached neural-like cells and colonies during the first 3-5 days (FIG. 1A). After careful removal of the unattached cells and cellular debris, these neural-like cells proliferated and rounded-up to form primary neuroshperes that grew in suspension after 3 weeks (FIG. 1A). Upon passaging, the neurospheres were trypsinized into single cells, and cells proliferated and reformed neurospheres in suspension with each passage (FIG. 1B). The diameter of the neurospheres ranged from approximately 50 to 100 nm, and they possessed the classic microspikes on their outer surface (FIG. 1B). These AF-NSCs could be expanded by continual passaging. It is important to note that AF-NSCs could only be established from amniotic fluid samples taken from NTD patients diagnosed with anencephaly (Table 1). AF-NSC lines could be established from 4 out of the 6 anencephaly samples (success rate 67%), and all 4 lines had a normal karyotype (FIG. 6).

TABLE 1

Sources and outcome of amniotic fluid samples.

| Patient Status | Total samples | # of AF-NSCs obtained | Success rate (%) |
|---|---|---|---|
| No defect NTD | 7 | 0 | 0 |
| anencephaly | 6 | 4 | 67 |
| Non-anencephaly | 6 | 0 | 0 |

Figure 1C:
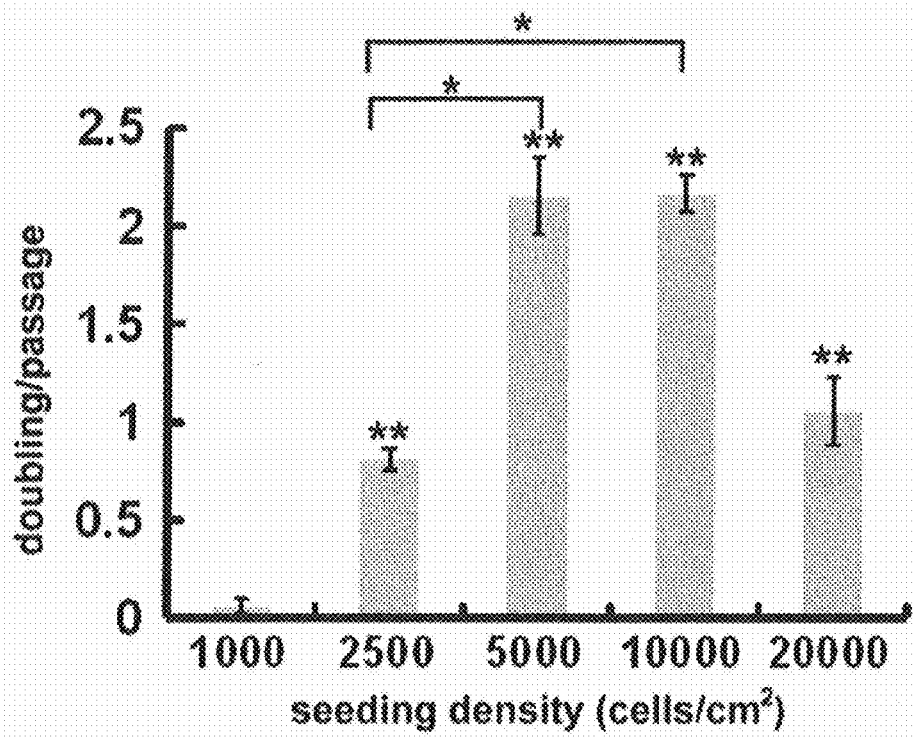
FIG. 1C shows the culture properties of AF-NSCs. The doubling time of AF-NSCs was affected by the seeding density. *: $p<0.05$; **: $p<0.01$.

The rate of neurosphere growth was influenced by the density at which the AF-NSCs were initially seeded. The optimal seeding density was determined to be 5,000-10,000 cells/cm$^2$ (FIG. 1C), with almost zero growth occurring at a density below 2,500 cells/cm$^2$. The AF-NSCs doubled at a rate of 109.4±14.8 hrs when they were plated at a density under 10,000 cells cells/cm$^2$.

Figure 1D:
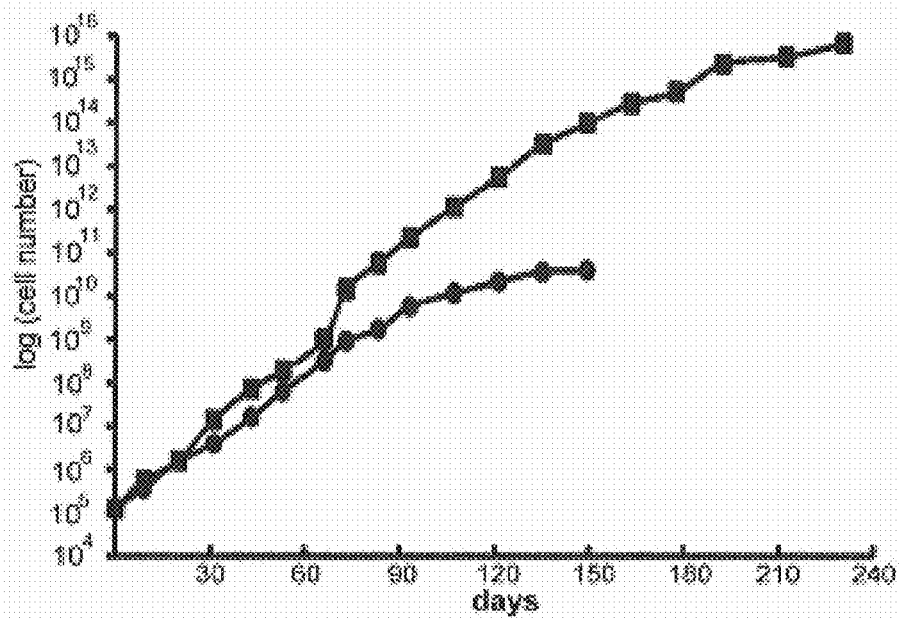
FIG. 1D shows the culture properties of AF-NSCs. AF-NSCs cell counts from long-term in vitro cultures. Two different AF-NSC lines were used for this analysis starting from passage 5, and the total cell number was calculated cumulatively at each passage. The two AF-NSCs lines, 100 and 106, were cultured for 18 and 23 passages, respectively. (Black square: AF-NSC line #100; black circle: AF-NSC line #106)

To test the long-term expansion potential of the AF-NSCs, we grew 2 different lines (starting at passage 5) in vitro over the course of several months. Both lines maintained constant growth for at least 5 months (FIG. 1D), and one line could be propagated for over 8 months. These two cell lines could be expanded over $10^5$-$10^{10}$-fold.

Example 2. Characterization of the AF-NSCs

Figure 2A:
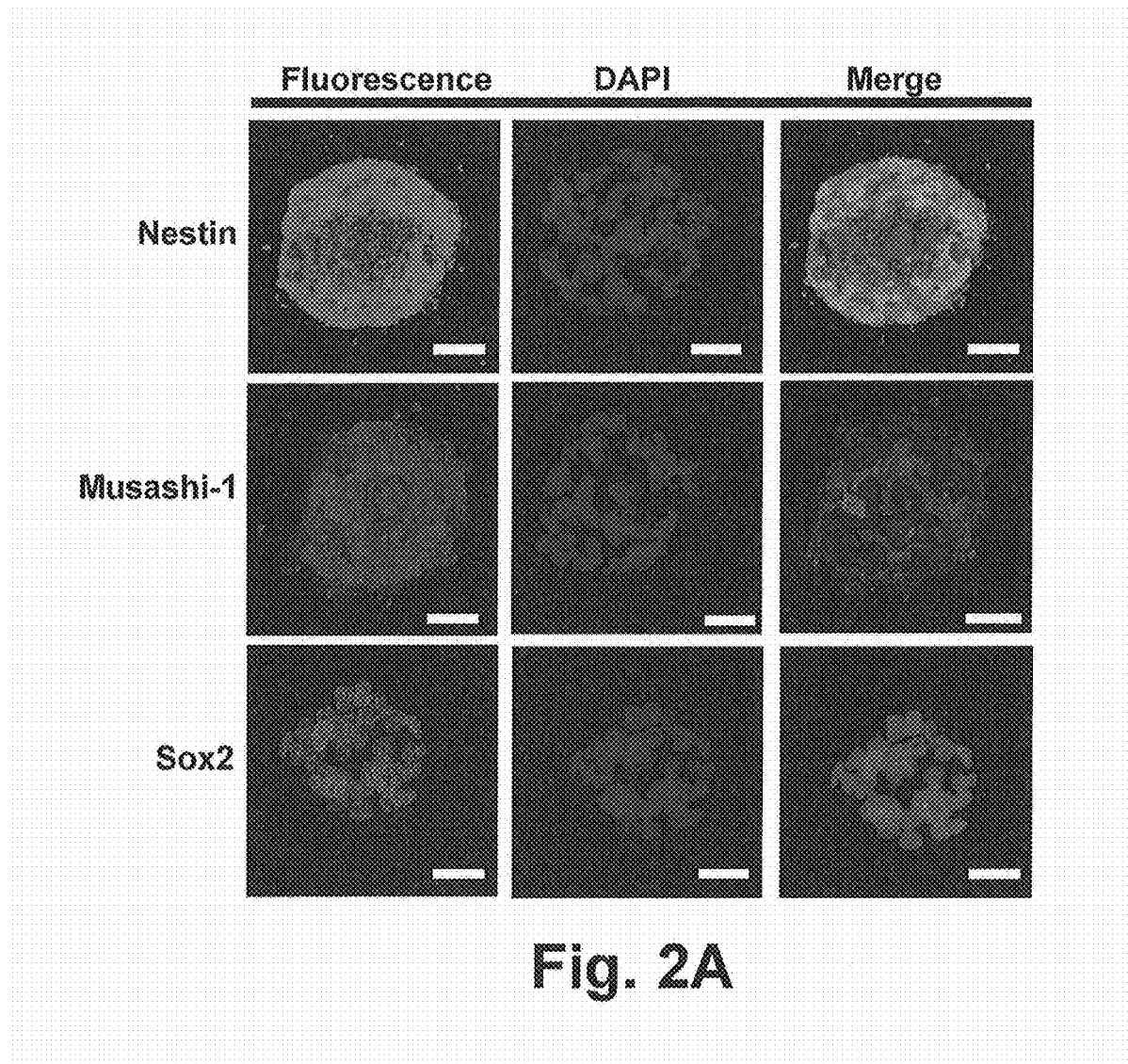
FIG. 2A shows the expression of NSC-specific markers in AF-NSCs. Confocal images of immunostained mature neurospheres (Day 14) revealed the expression of specific NSC markers (Nestin, Musashi-1 and Sox2). Scale bar: 20 µm.

To characterize the AF-NSCs, immunocytochemistry and flow cytometry were used to detect the expression NSC-specific markers. Confocal microscopy revealed that AF-NSC-derived neurospheres strongly expressed both Nestin and Musashi-1 within cytoplasm. Sox2, a nucleus protein, could also be observed in the neurospheres (FIG. 2A).

Figure 2B:
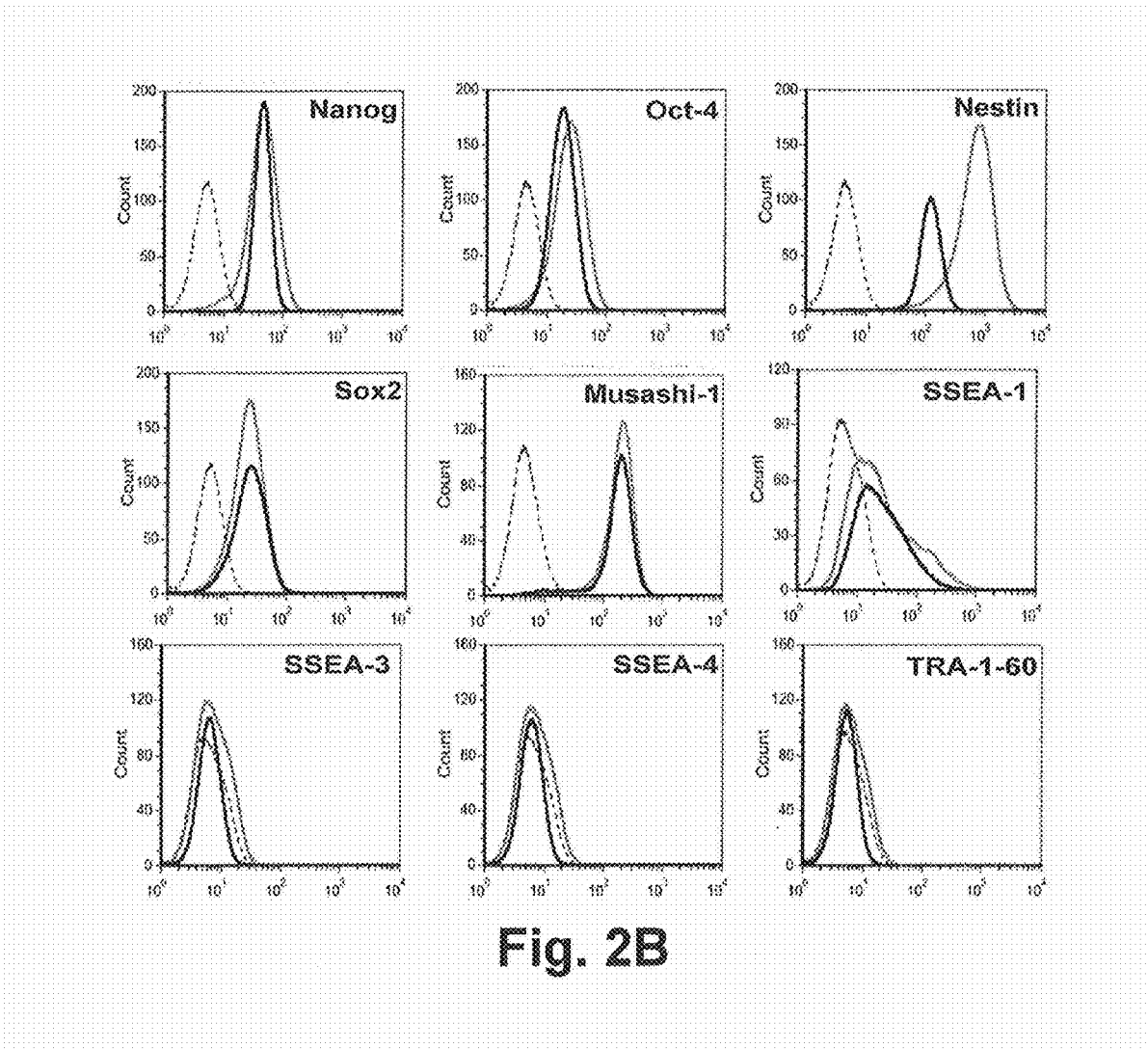
FIG. 2B shows the expression of NSC-specific markers in AF-NSCs. The expression of NSC-specific cell markers in AF-NSCs was determined by flow cytometry at early and late passage numbers. Dotted line: isotype antibody control; gray line: early passage #(10-12); black line: late passage #(20-22). Abbreviations: SSEA: stage-specific embryonic antigen; ABCG2: ATP-binding cassette sub-family G2; HLA: human leukocyte antigen.
Figure 2B:
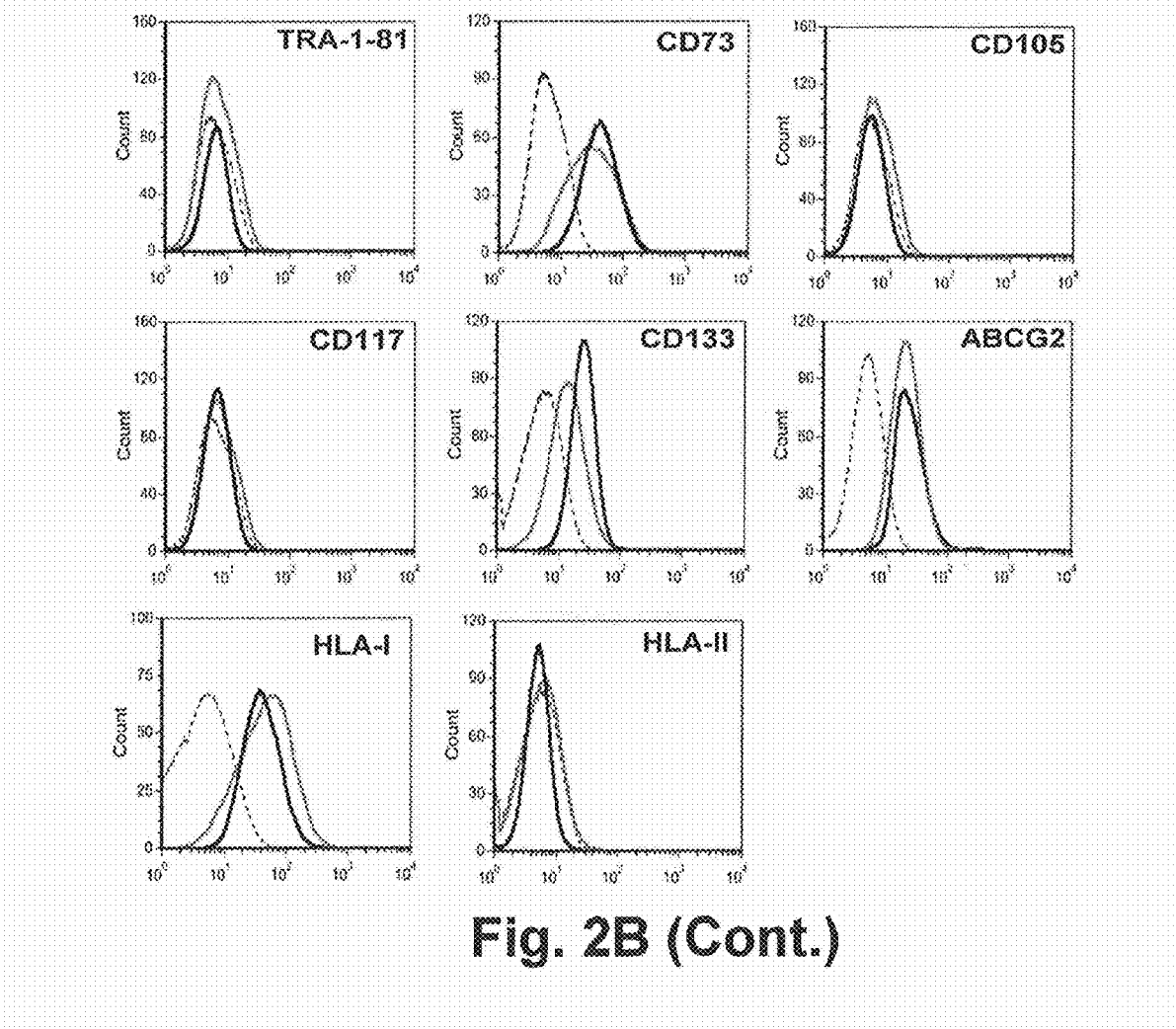

Flow cytometry revealed that AF-NSCs express NSC-specific markers Nestin, Sox2, Musashi-1 and ABCG2 (FIG. 2B). CD133 was initially expressed at a low level, but the intensity of the signal increased with subsequent passages. We also analyzed the expression of embryonic stem (ES) cell-specific markers and determined that our AF-NSCs expressed a similar set of the transcription factors to ES cells, including Nanog, Oct-4, and Sox2, and low levels of SSEA-1; however, they did not express SSEA-3, SSEA-4, TRA-1-60, and TRA-81. Furthermore, the pattern of human leukocyte antigen (HLA) expression in AF-NSCs was similar to most stromal cells, which express HLA class I but not HLA class II. When compared to mesenchymal stem cells from amniotic fluid, which express CD73, CD105 and occasionally CD117, our AF-NSCs did not express either CD105 or CD117 and only occasionally expressed CD73. Interestingly, the expression pattern of all markers which we detected was maintained in AF-NSCs throughout their time in vitro (through passage #20-22).

Figure 2C:
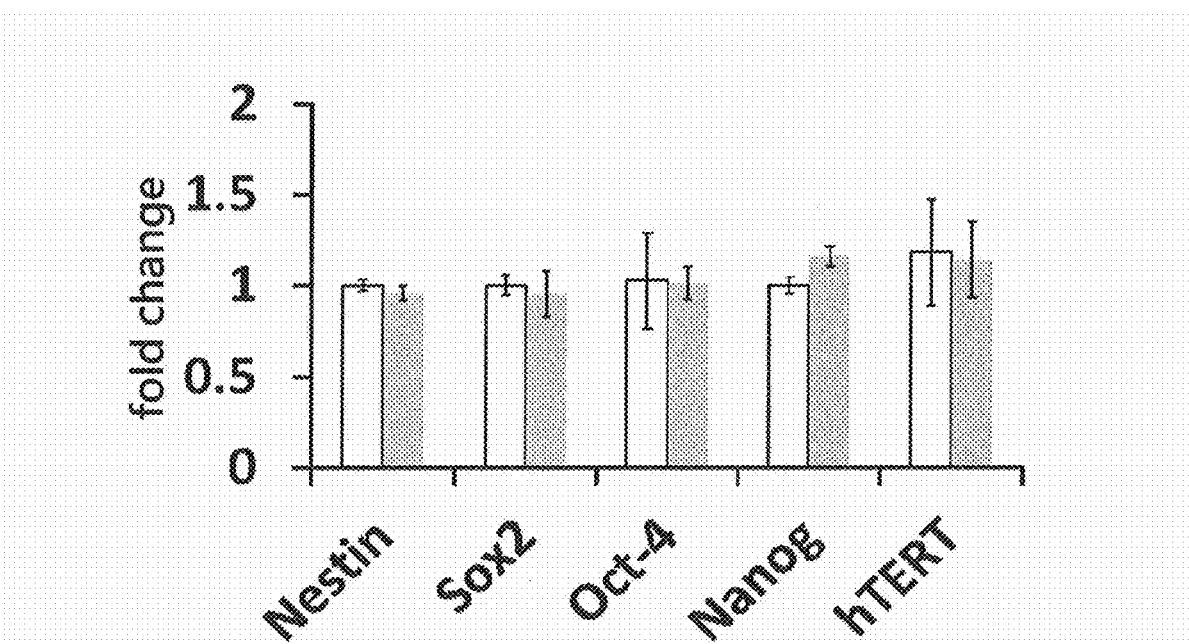
FIG. 2C shows the expression of NSC-specific markers in AF-NSCs. qPCR was used to determine mRNA levels of NSC-specific genes at early and late passages. White bar: early passage #10; gray bar: late passage #20.
Figure 2D:
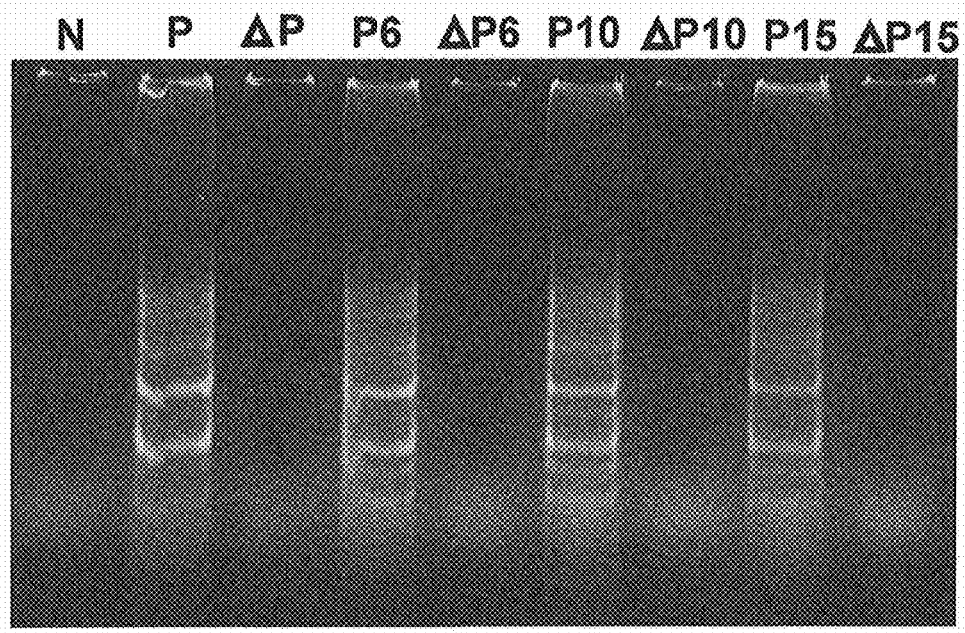
FIG. 2D shows the measurement of telomerase activity in AF-NSCs. Telomerase activity was measured at different times in culture (passage #6, 10 and 17). The triangle designates samples that were treated by heat inactivation. Abbreviations: N: negative control; P: positive control.

We also employed qPCR to measure the expression levels of these markers throughout multiple passages and found that Nestin, Sox2, Oct-4, Nanog and hTERT were all consistently expressed over the course of 20 passages (FIG. 2C), which confirmed our previous observations with flow cytometry. Finally, we assessed the telomerase activity of our AF-NSCs and determined that the activity levels were maintained despite increasing passage numbers in long-term cultures (FIG. 2D).

Example 3. In Vitro Neural Differentiation of AF-NSCs

Figure 3A:
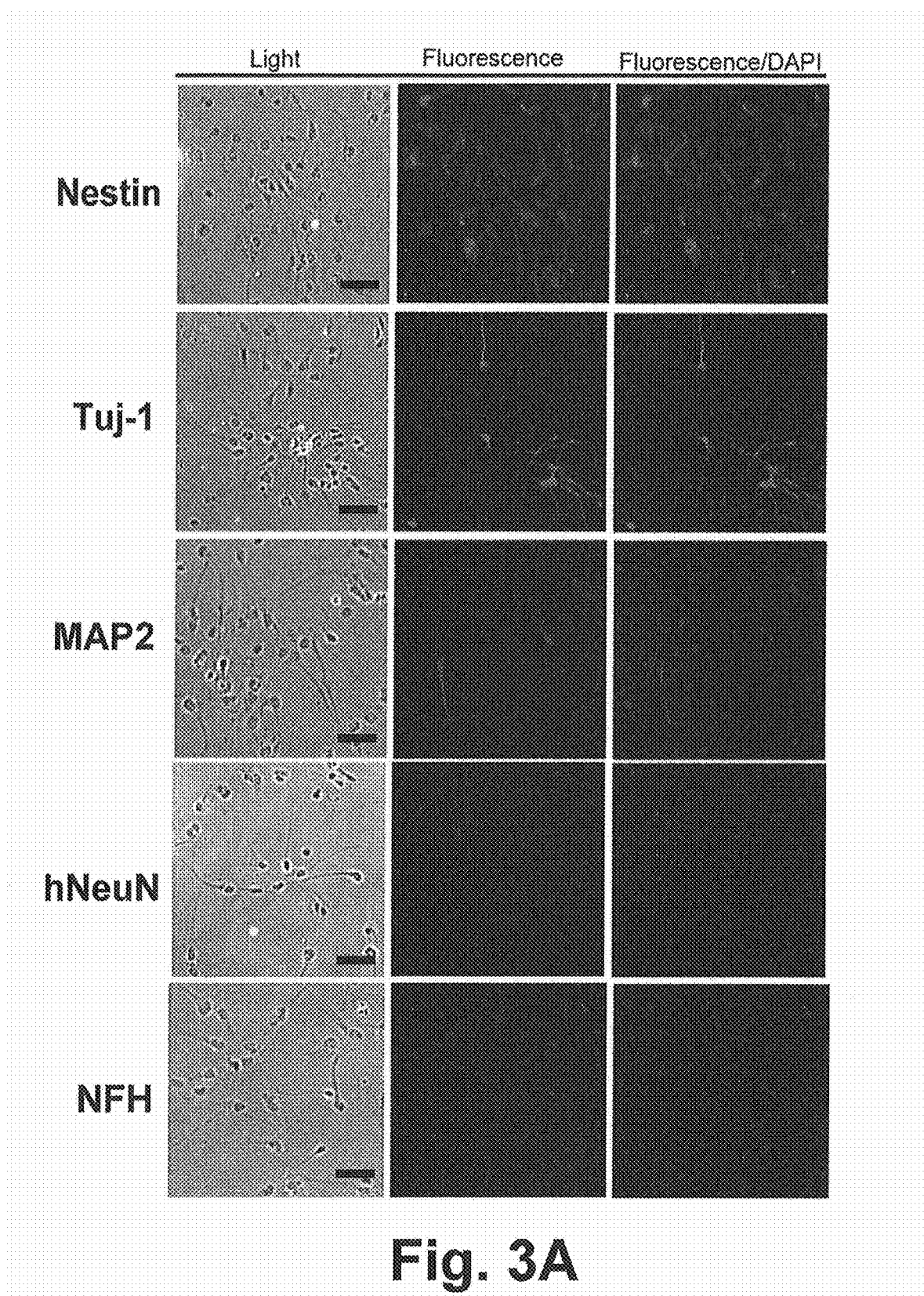
FIG. 3A shows in vitro differentiation of AF-NSCs. The AF-NSCs were cultured in neural differentiation medium, and markers of early and mature neurons were detected by immunocytochemistry at 2 days post-induction. Scale bar: 20 µm. Abbreviations: DAPI: 4',6-diamidino-2-phenylindole.
Figure 3B:
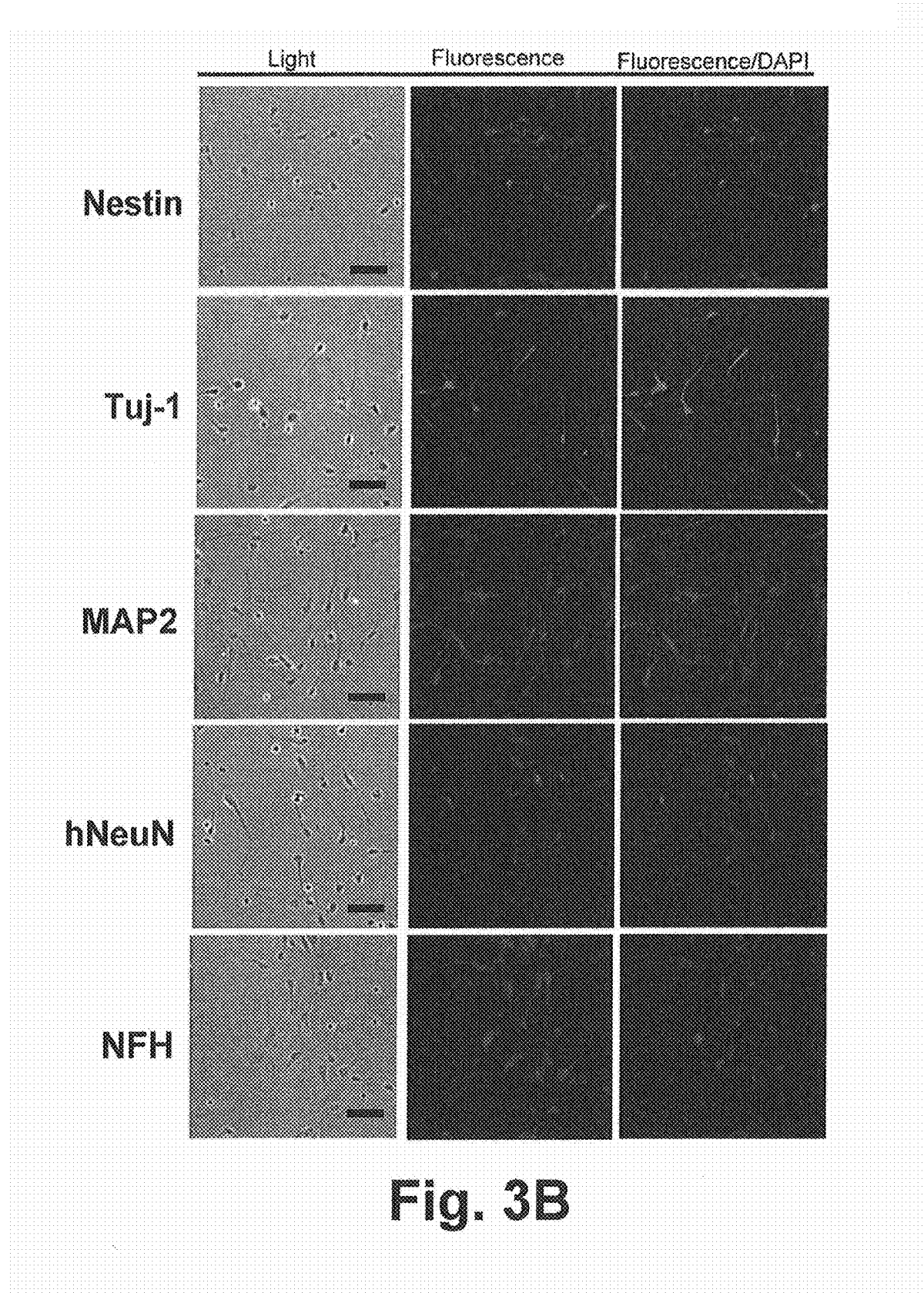
FIG. 3B shows in vitro differentiation of AF-NSCs. The AF-NSCs were cultured in neural differentiation medium, and markers of early and mature neurons were detected by immunocytochemistry at 7 days post-induction. Scale bar: 20 µm. Abbreviations: DAPI: 4',6-diamidino-2-phenylindole.
Figure 3C:
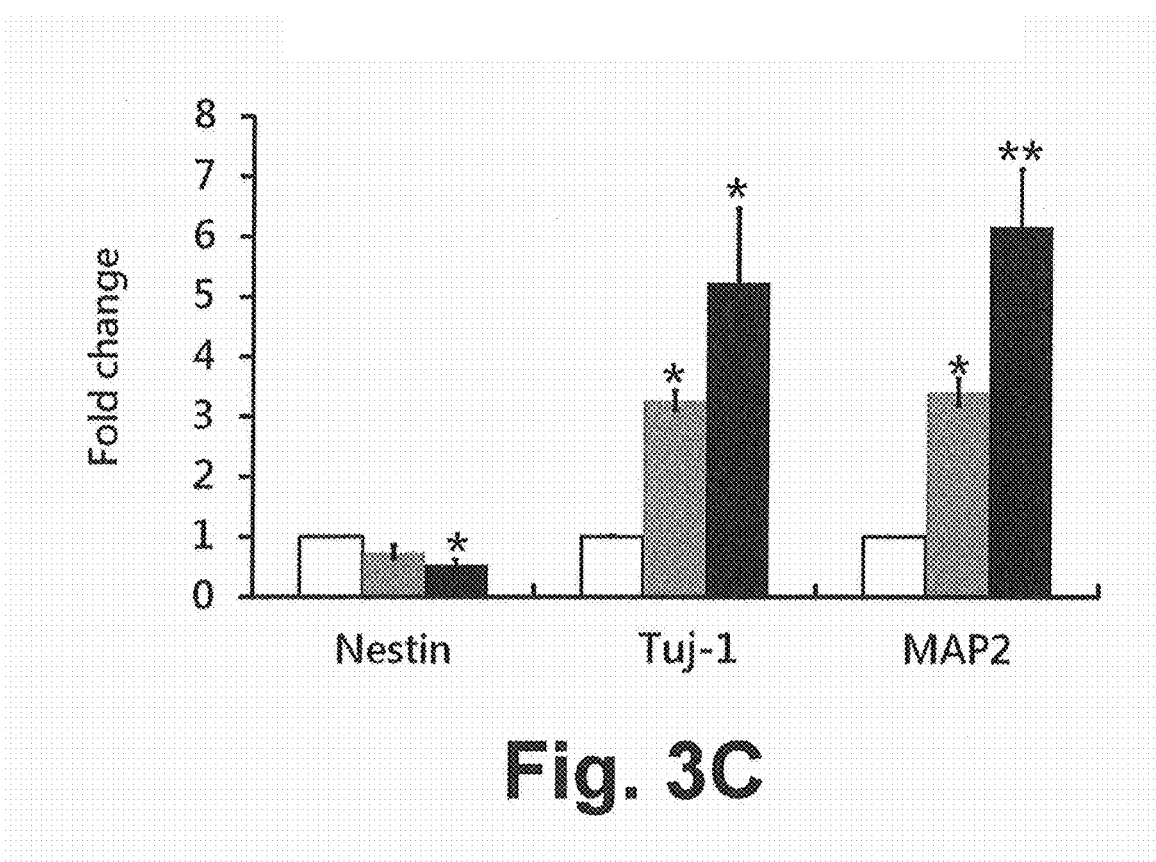
FIG. 3C shows the expression of neuronal specific genes after in vitro differentiation of AF-NSCs. qPCR was used to measure the expression levels of these neuronal markers. White bar: undifferentiated cells; gray bar: differentiated cells at day 2; black bar: differentiated cells at day 7. *: $p<0.05$; **: $p<0.01$.

To determine whether AF-NSCs could differentiate into neurons, the cells were dissociated into a single cell suspension, cultured in NeuroCult™ differentiation medium and subsequently analyzed by immunocytochemistry. After 2 days of induction, the AF-NSCs began to undergo morphological changes, and only Nestin and Tuj-1 were expressed within cells at this stage (FIG. 3A). Additional neuron-specific markers, including Nestin, Tuj-1, MAP2, hNeuN and NFH, could be detected after 7 days of induction (FIG. 3B). We also used qPCR to determine the transcription levels of these neuron-specific genes and found that Tuj-1 and MAP2 were upregulated by 5.2- and 6.2-fold, respectively, after 7 days of differentiation. In contrast, the expression of Nestin, a NSC-specific gene, significantly decreased during this same time period (FIG. 3C).

Figure 4A:
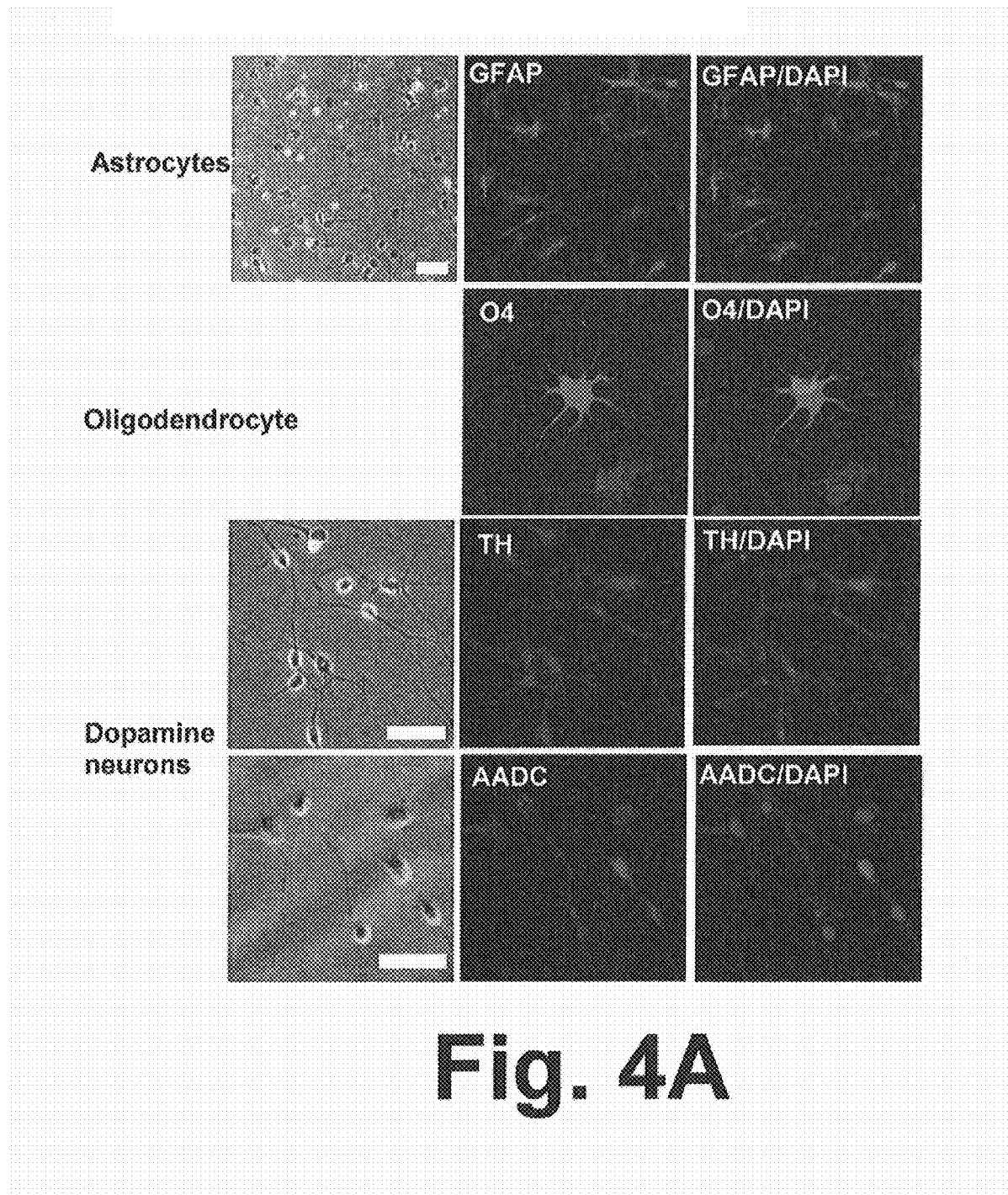
FIG. 4A shows directed differentiation of AF-NSCs into astrocytes, oligodendrocytes and dopaminergic neurons. AF-NSCs were cultured in specific differentiation medium and immunostained for specific markers to confirm the presence of astrocytes (GFAP), oligodendrocytes (04) and dopaminergic neurons (TH and AADC). Scale bar: 20 µm. Abbreviations: GFAP: glial fibrillary acidic protein; TH: tyrosine hydroxylase; AADC: aromatic L-amino acid decarboxylase; and DAPI: 4',6-diamidino-2-phenylindole.
Figure 4B:
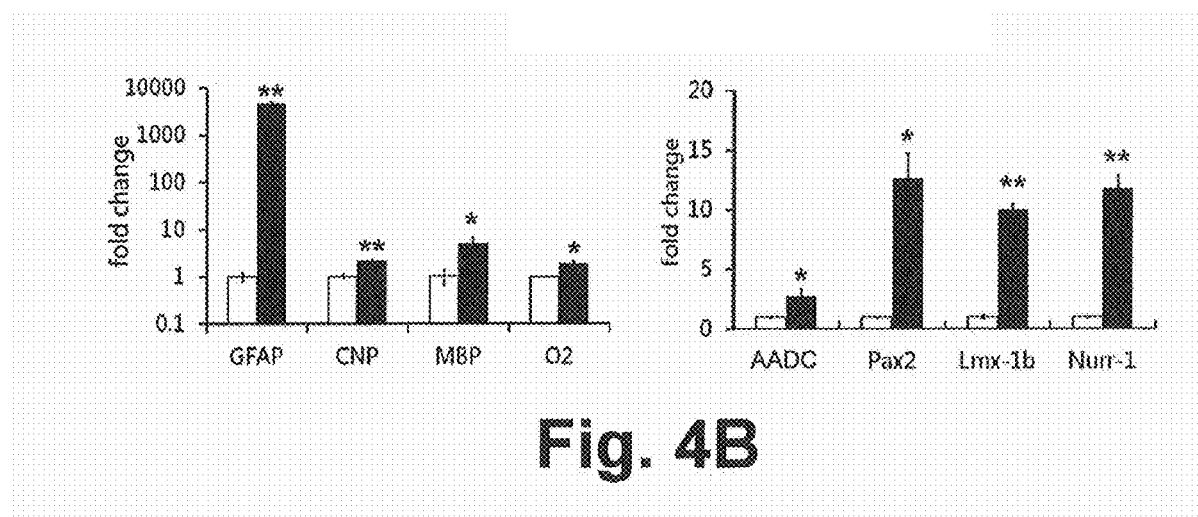
FIG. 4B shows the expression of specific markers of differentiated AF-NSCs. qPCR was used to analyze gene expression of astrocyte (GFAP), oligodendrocyte (CNP, MBP and 02) (left) and dopaminergic neuron (AADC, Pax2, Lmx-1b and Nurr-1) (right) specific markers. White bar: before differentiation; black bar: after differentiation. *: $p<0.05$; **: $p<0.01$. Abbreviations: GFAP: glial fibrillary acidic protein.

Next, we induced our AF-NSCs into astrocytes, oligodendrocytes and dopaminergic neurons by exposing them to defined differentiation media. Most (>80%) AF-NSCs could be induced to become GFAP positive astrocytes (FIG. 4A) as determined by the dramatic 4,700-fold increase in GFAP expression after 2 weeks of induction (FIG. 4B). Oligodendrocytes were detected by immunostaining for O4 antigen (FIG. 4A). Compared with undifferentiated AF-NSCs, induction in defined medium caused the expression of the oligodendrocyte-specific genes CNP, MBP and O2 to increase to 2.15-, 4.97- and 1.9-fold, respectively. Moreover, the presence of TH- and AADC-positive cells after 1 month suggested that AF-NSCs could give rise to dopaminergic neurons (FIG. 4A). This observation was verified by qPCR analysis, which determined that markers specific for dopaminergic neuron, including AADC, Pax2, Lmx-1b and Nurr-1, were significantly upregulated after differentiation (FIG. 4B).

Example 4. AF-NSCs were Transplanted into Ischemia Rats and Induced Functional Recovery To determine whether AF-NSCs could induce functional recovery from stroke in vivo, 1×10$^6$ cells were transplanted into the ischemic boundary zone of a rat brain that had undergone MCAO. Non-treated rats with an MCAO consistently showed impaired motor performance when compared to healthy control as assessed by the rotarod and grip strength tests.

Figure 5A:
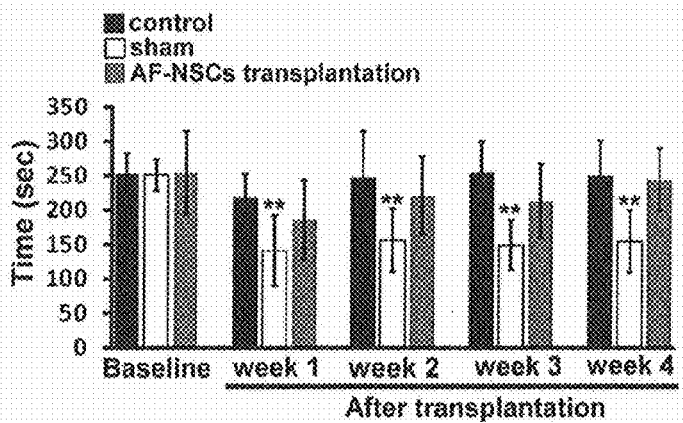
FIG. 5A shows engrafting AF-NSCs into MCAO ischemic rats has therapeutic effects. After AF-NSCs were transplanted, ischemia rats underwent a rotarod test. Black bar: healthy control; white bar: sham control; gray bar: AF-NSC transplantation after MCAO.

In the rotarod test, the MCAO group that was treated with AF-NSCs experienced a 43±18% reduction in time when compared to sham-injected MCAO control rats, which suggests that the presence of AF-NSCs improved the motor deficits observed in ischemic rats. Notably, the AF-NSCs promoted rapid recovery of motor function during the first week post-injection (85±26%), and this improvement was maintained for 4 weeks post-engraftment (98±18%; FIG. 5A).

Figure 5B:
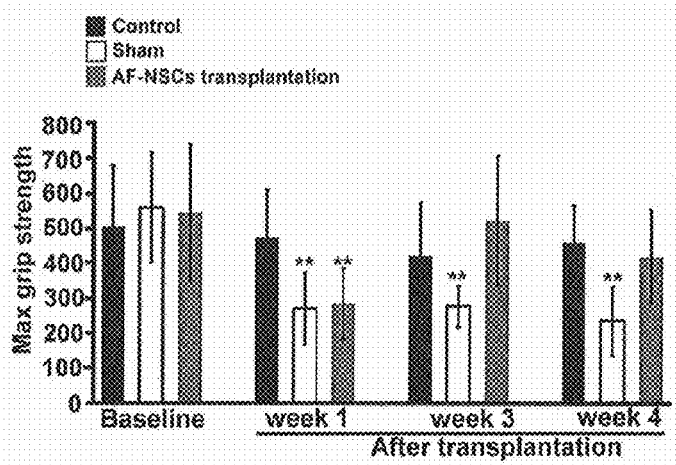
FIG. 5B shows engrafting AF-NSCs into MCAO ischemic rats has therapeutic effects. After AF-NSCs were transplanted, ischemia rats underwent a grip strength test. Black bar: healthy control; white bar: sham control; gray bar: AF-NSC transplantation after MCAO.

A similar improvement in function was observed with the grip strength test (FIG. 5B). Experiencing an MCAO significantly decreased the rat's maximum grip strength. One week after they received a transplant of AF-NSCs, the maximum grip strength of these ischemic rats was similar to that of the sham-operated control group. However, the rats that received AF-NSCs could recover their normal grip strength 3 to 4 weeks post-transplantation, whereas the sham-operated controls remained weak.

Figure 5C:
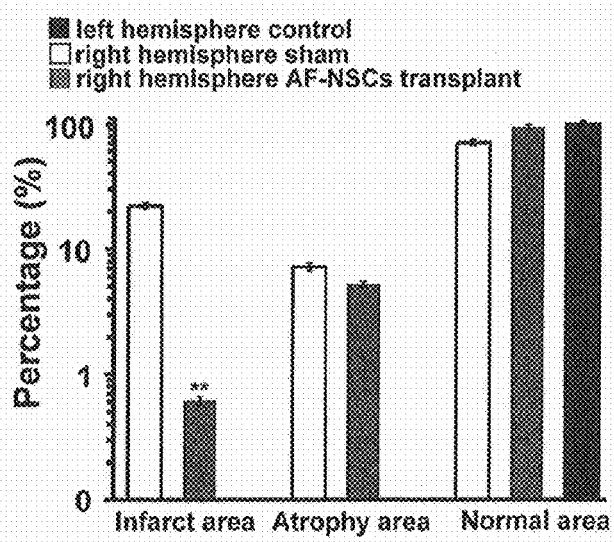
FIG. 5C shows engrafting AF-NSCs into MCAO ischemic rats has therapeutic effects. Quantification of the hemispheric lesion area by TTC 4 weeks after AF-NSC transplantation.
Figure 5D:
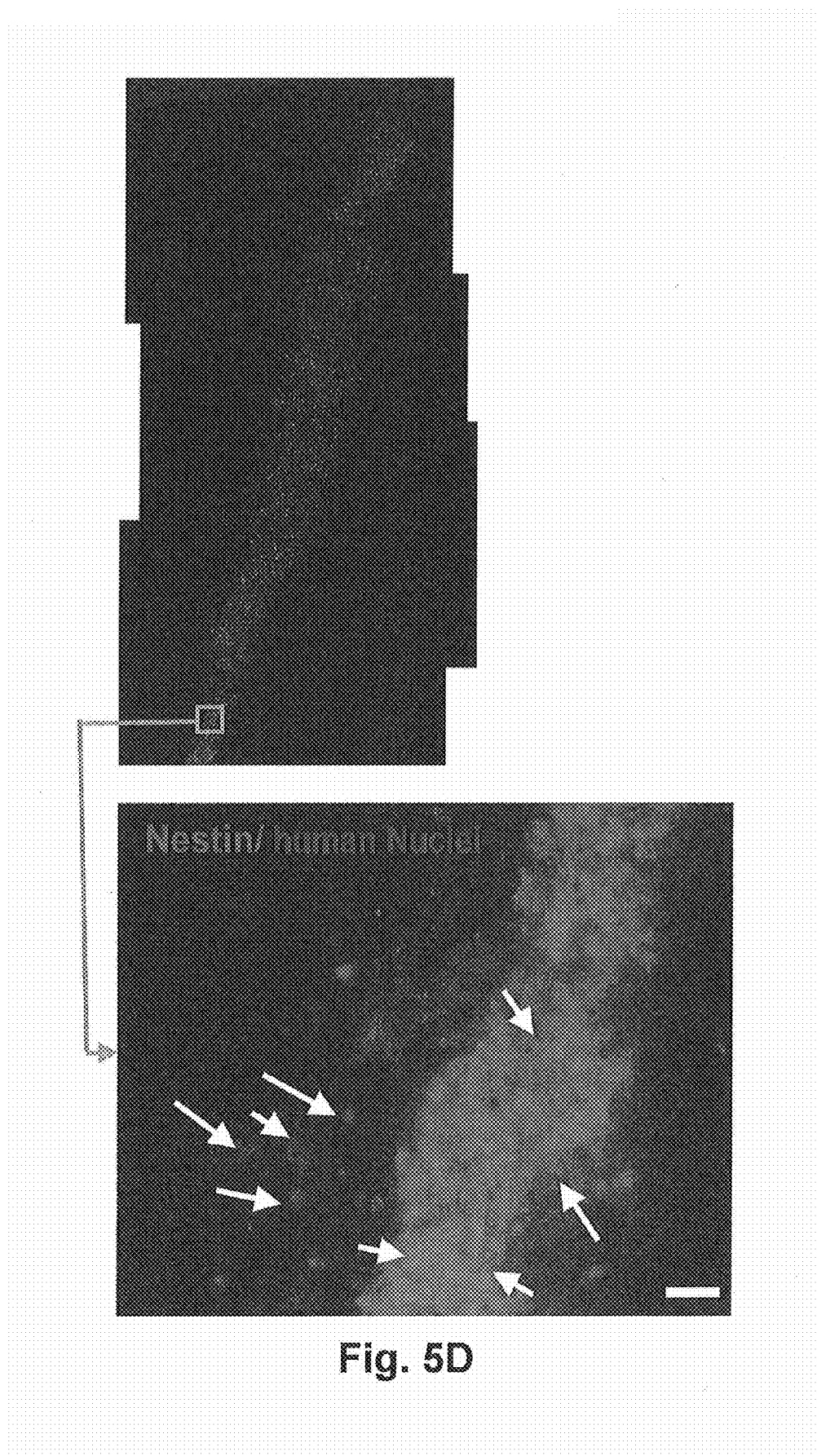
FIG. 5D shows engrafting AF-NSCs into MCAO ischemic rats has therapeutic effects. Top: Immunohistochemistry revealed Nestin (green) expression in the injection region. Bottom: Higher magnification of this region revealed that grafted AF-NSCs co-express Nestin (green) and human Nuclei (red, arrows) in the damaged area. Scale bar: 50 µm.

To determine the extent of damage after MCAO, the engrafted brains were stained with TTC 4 weeks after the AF-NSCs transplant. The size of the infarcted area was significantly reduced after transplantation (sham: 22.17±1.12%; AF-NSCs transplanted: 0.62±0.15%), whereas the atrophied region remained the same (sham: 7.21±0.48%; AF-NSCs transplanted: 5.26±0.57%; FIG. 5C). We then used immunohistochemistry to determine whether the AF-NSCs survived in the rat's brain after being transplanted by double labeling cryosections with antibodies against Nestin and human Nuclei antibodies. Our results showed that the Nestin/human nuclei double positive cells were located close the injection area (FIG. 5D), which suggests that the engrafted AF-NSCs could survive and integrated into the host brain.

Discussion

Over the past two decades, primary neural stem cells have been isolated from both the fetal and adult CNS. Recent studies have suggested that cells with the potential to become neurons can also be found in amniotic fluid [23, 25, 29]; however, human neural stem cells have not yet been isolated and cultured from this location. Turner et al. reported that NSCs could be isolated and cultured from amniotic fluid of Sprague-Dawley rats that had undergone prenatal exposure to retinoic acid that resulted in NTDs; however, these cells were absent in healthy control rats [26]. These AF-derived cells exhibited typical neural progenitor morphology and robustly expressed the NSC-specific markers Nestin and Sox-2. Previous studies have also reported that there is a statistically significant increase in the number of neural stem cells that can be derived from the amniotic fluid of rats with spina bifida when compared to those animals with exencephaly alone or with both spina bifida and exencephaly [30]. In this study, we were able to isolate AF-NSCs from human amniotic fluid collected from fetuses that had been diagnosed with anencephaly (67%) but not from normal patients or from those with a non-anencephaly NTD. These results suggest that the proportion of neural stem cells in amniotic fluid is higher in those fetuses with an NTD, specifically anencephaly. Anencephaly occurs when the anterior neural tube fails to close and results in a total or partial absence of the cranial vault and cerebral hemispheres. The outward flow of cerebrospinal fluid into the amniotic fluid was also used in diagnosing an NTD [30-32]. We argue that the presence of neural stem cells in the amniotic fluid could be caused by leakage from the exposed neural tissues and/or the cerebrospinal fluid into the amniotic cavity.

Neural stem cells can self-renew and differentiate into all CNS cell types and are typically grown as neurospheres under serum-free conditions in vitro [33]. In our study, all 4 AF-NSC lines that we established could be maintained as neurospheres for more than 5 months and developed typical microspikes on their surface. Previous studies have suggested that neural precursor cells isolated from human embryo have decreased telomerase activity, which declines to an undetectable level after 20 population doublings [34]. Conversely, our AF-NSCs could be expanded over several months and maintained their telomerase activity even at later passage numbers. However, although they maintained their telomerase activity, AF-NSCs did not form teratomas in vivo. Typical human NSCs cells isolated from various CNS structures in 6-14.5 week-old human fetuses experienced a long doubling time (8-10 days) in vitro [35]. Comparatively, our AF-NSCs divided every 4-5 days. Because the growth of NSCs is affected by cell density due to the additional cell-cell interactions, the number of neurospheres is greater at higher cell density than at low cell density [36, 37]. We found that AF-NSCs remained in a quiescent state (<1 doubling/passage) when seeded at low densities (<2,500 cells/cm$^2$), whereas they would continue to proliferate under conditions of higher cell density cultures (5,000-10,000 cells/cm$^2$). However, the cells could not grow when the density was too high (>20,000 cells/cm$^2$).

Nestin, Sox2, ABCG2, SSEA-1 and Musashi-1 have all been previously established as NSC-specific markers [38, 39]. Our AF-NSCs maintained their expression of these markers during long-term cultivation in vitro. CD133 is a cell surface marker used to isolated hematopoietic stem cells and neural stem cells [40]. In this study, the expression of CD133 increased in the AF-NSCs throughout their time in culture. Amniotic fluid has been identified as an ideal source to isolate fetal multipotent stem cells (AFSCs) [24, 41]. AFSCs share some markers with mesenchymal stem cells, such as CD73, CD105 and CD117, and with pluripotent stem cells, such as Oct-4, Nanog, and Sox2 etc. However, AF-NSCs did not express either CD105 or CD117, and only expressed CD73 on their surface. While AF-NSCs did express Nanog and Oct-4, they did not stain for any embryonic stem cell markers, including SSEA-3, SSEA-4, TRA-1-60 and TRA-1-81. Taken together, these results suggest that AF-NSCs are distinct from previously identified AFSCs.

Another hallmark of NSCs is their ability to differentiate into multiple CNS cell types. We have demonstrated that AF-NSCs have the potential to become neurons, astrocytes, oligodendrocytes, and dopaminergic neurons in vitro. During oligodendrocyte development, O4 is expressed in both oligodendrocyte precursors and mature oligodendrocytes, whereas CNP and MBP are only expressed in mature myelinating oligodendrocytes [42]. AF-NSCs could be induced into O4 immunoreactive cells successfully in vitro; however, these cells did not express either CNP or MBP at the protein level (data not shown), although a significant increase in mRNA could be detected by qPCR in multiple AF-NSC lines. This discrepancy may reflect a need for further stimulation in vitro to produce mature oligodendrocytes. Previous studies have demonstrated that brain-derived NSCs can differentiate into neurons and provide functional improvement in the behavior of ischemic rats [43-44]. Like fetal NSCs, undifferentiated AF-NSCs can be grafted efficiently near the lesioned region in a rat stroke model. Furthermore, AF-NSCs can induce a recovery of the ischemia-induced reduction in grip-strength and rotarod performance. One hypothesis is that NSC transplantation might induce tissue repair because these cells attenuate inflammation, increase anti-apoptotic activity or reduce infarct size [43, 45]. Here, we observed a marked reduction of infarct size in ischemic rats after the injection of AF-NSCs. Taken together, these results suggest that the AF-NSCs not only have the potential to differentiate in vitro but also have a neuroprotective effect on ischemic rats.

The main obstacles in using human NSCs for cellular therapy have typically been the limitation of available sources, complicated isolation protocols and time-consuming expansion. In this study, we have demonstrated AF-NSCs derived from patients with an NTD can be isolated and expanded ex vivo and exhibit similar physiological characters to other sources of NSCs. Using high resolution ultrasonography and amniocentesis to detect an NTD during pregnancy would allow human AF-NSCs to be efficiently collected. Therefore, human AF-NSC banks could be established for clinical and preclinical testing purposes.

CONCLUSION

In conclusion, AF-NSCs derived from fetuses with NTDs share common characteristics with other sources of human NSCs, including the ability to from neurospheres, expression of stem cell-specific makers, the ability to undergo long-term proliferation, the potential to differentiate in vitro and the potential to have therapeutic effects in a rat stroke model. Therefore, this novel source of human NSCs could have a significant impact on future translational and therapeutic studies.

REFERENCES

1. Okano H. Neural stem cells: progression of basic research and perspective for clinical application. *The Keio journal of medicine.* 2002; 51:115-128.
2. Reynolds B A, Weiss S. Generation of neurons and astrocytes from isolated cells of the adult mammalian central nervous system. *Science.* 1992; 255:1707-1710.
3. Kordower J H, Freeman T B, Snow B J et al. Neuropathological evidence of graft survival and striatal reinnervation after the transplantation of fetal mesencephalic tissue in a patient with Parkinson's disease. *The New England journal of medicine.* 1995; 332:1118-1124.
4. Hwang D H, Lee H J, Park I H et al. Intrathecal transplantation of human neural stem cells overexpressing VEGF provide behavioral improvement, disease onset delay and survival extension in transgenic ALS mice. *Gene therapy.* 2009; 16:1234-1244.
5. Andres R H, Horie N, Slikker W et al. Human neural stem cells enhance structural plasticity and axonal transport in the ischaemic brain. *Brain: a journal of neurology.* 2011; 134:1777-1789.
6. Abematsu M, Tsujimura K, Yamano M et al. Neurons derived from transplanted neural stem cells restore disrupted neuronal circuitry in a mouse model of spinal cord injury. *The Journal of clinical investigation.* 2010; 120:3255-3266.
7. Gonzalez-Perez O. Neural stem cells in the adult human brain. *Biological and biomedical reports.* 2012; 2:59-69.
8. Schwartz P H, Bryant P J, Fuja T J et al. Isolation and characterization of neural progenitor cells from post-mortem human cortex. *Journal of neuroscience research.* 2003; 74:838-851.
9. Vescovi A L, Parati E A, Gritti A et al. Isolation and cloning of multipotential stem cells from the embryonic human CNS and establishment of transplantable human neural stem cell lines by epigenetic stimulation. *Experimental neurology.* 1999; 156:71-83.
10. Earl C D, Reum T, Xie J X et al. Foetal nigral cell suspension grafts influence dopamine release in the non-grafted side in the 6-hydroxydopamine rat model of Parkinson's disease: in vivo voltammetric data. *Experimental brain research.* 1996; 109:179-184.
11. Ryder E F, Snyder E Y, Cepko C L. Establishment and characterization of multipotent neural cell lines using retrovirus vector-mediated oncogene transfer. *Journal of neurobiology.* 1990; 21:356-375.
12. De Filippis L, Ferrari D, Rota Nodari L et al Immortalization of human neural stem cells with the c-myc mutant T58A. *PloS one.* 2008; 3:e3310.
13. Zhang S C, Wernig M, Duncan I D et al. In vitro differentiation of transplantable neural precursors from human embryonic stem cells. *Nature biotechnology.* 2001; 19:1129-1133.
14. Reubinoff B E, Itsykson P, Turetsky T et al. Neural progenitors from human embryonic stem cells. *Nature biotechnology.* 2001; 19:1134-1140.
15. Chambers S M, Fasano C A, Papapetrou E P et al. Highly efficient neural conversion of human ES and iPS cells by dual inhibition of SMAD signaling. *Nature biotechnology.* 2009; 27:275-280.
16. Miura K, Okada Y, Aoi T et al. Variation in the safety of induced pluripotent stem cell lines. *Nature biotechnology.* 2009; 27:743-745.
17. Botto L D, Moore C A, Khoury M J et al. Neural-tube defects. *The New England journal of medicine.* 1999; 341:1509-1519.
18. Copp A J, Greene N D. Genetics and development of neural tube defects. *The Journal of pathology.* 2010; 220:217-230.
19. Copp A J, Stanier P, Greene N D. Neural tube defects: recent advances, unsolved questions, and controversies. *Lancet neurology.* 2013; 12:799-810.
20. Yamaguchi Y, Miura M. How to form and close the brain: insight into the mechanism of cranial neural tube closure in mammals. *Cellular and molecular life sciences: CMLS.* 2013; 70:3171-3186.
21. Kennedy D, Chitayat D, Winsor E J et al. Prenatally diagnosed neural tube defects: ultrasound, chromosome, and autopsy or postnatal findings in 212 cases. *American journal of medical genetics.* 1998; 77:317-321.
22. Wald N, Cuckle H, Nanchahal K. Amniotic fluid acetylcholinesterase measurement in the prenatal diagnosis of open neural tube defects. Second report of the Collaborative Acetylcholinesterase Study. *Prenatal diagnosis.* 1989; 9:813-829.
23. Tsai M S, Lee J L, Chang Y J et al. Isolation of human multipotent mesenchymal stem cells from second-trimester amniotic fluid using a novel two-stage culture protocol. *Hum Reprod.* 2004; 19:1450-1456.
24. De Coppi P, Bartsch G, Jr., Siddiqui M M et al. Isolation of amniotic stem cell lines with potential for therapy. *Nature biotechnology.* 2007; 25:100-106.
25. Prusa A R, Marton E, Rosner M et al. Neurogenic cells in human amniotic fluid. *American journal of obstetrics and gynecology.* 2004; 191:309-314.
26. Turner C G, Klein J D, Wang J et al. The amniotic fluid as a source of neural stem cells in the setting of experimental neural tube defects. *Stem cells and development.* 2013; 22:548-553.
27. Swistowski A, Peng J, Liu Q et al. Efficient generation of functional dopaminergic neurons from human induced pluripotent stem cells under defined conditions. *Stem Cells.* 2010; 28:1893-1904.
28. Longa E Z, Weinstein P R, Carlson S et al. Reversible middle cerebral artery occlusion without craniectomy in rats. *Stroke; a journal of cerebral circulation.* 1989; 20:84-91.
29. McLaughlin D, Tsirimonaki E, Vallianatos G et al. Stable expression of a neuronal dopaminergic progenitor phenotype in cell lines derived from human amniotic fluid cells. *Journal of neuroscience research.* 2006; 83:1190-1200.
30. Pennington E C, Gray F L, Ahmed A et al. Targeted quantitative amniotic cell profiling: a potential diagnostic tool in the prenatal management of neural tube defects. *Journal of pediatric surgery.* 2013; 48:1205-1210.
31. McComb J G. Spinal and cranial neural tube defects. *Seminars in pediatric neurology.* 1997; 4:156-166.
32. Emery A E, Brock D J, Burt D et al. Amniotic fluid composition in malformations of the fetal central nervous system. *The Journal of obstetrics and gynaecology of the British Commonwealth.* 1974; 81:512-516.

33. Reynolds B A, Rietze R L. Neural stem cells and neurospheres—re-evaluating the relationship. *Nature methods.* 2005; 2:333-336.
34. Ostenfeld T, Caldwell M A, Prowse K R et al. Human neural precursor cells express low levels of telomerase in vitro and show diminishing cell proliferation with extensive axonal outgrowth following transplantation. *Experimental neurology.* 2000; 164:215-226.
35. De Filippis L, Lamorte G, Snyder E Y et al. A novel, immortal, and multipotent human neural stem cell line generating functional neurons and oligodendrocytes. *Stem Cells.* 2007; 25:2312-2321.
36. Tropepe V, Sibilia M, Ciruna B G et al. Distinct neural stem cells proliferate in response to EGF and FGF in the developing mouse telencephalon. *Developmental biology.* 1999; 208:166-188.
37. Morshead C M, van der Kooy D. Disguising adult neural stem cells. *Current opinion in neurobiology.* 2004; 14:125-131.
38. Bauer H C, Tempfer H, Bernroider G et al. Neuronal stem cells in adults. *Experimental gerontology.* 2006; 41:111-116.
39. Capela A, Temple S. LeX/ssea-1 is expressed by adult mouse CNS stem cells, identifying them as nonependymal. *Neuron.* 2002; 35:865-875.
40. Sun Y, Kong W, Falk A et al. CD133 (Prominin) negative human neural stem cells are clonogenic and tripotent. *PloS one.* 2009; 4:e5498.
41. Tsai M S, Hwang S M, Tsai Y L et al. Clonal amniotic fluid-derived stem cells express characteristics of both mesenchymal and neural stem cells. *Biology of reproduction.* 2006; 74:545-551.
42. Zhang S C. Defining glial cells during CNS development. *Nature reviews Neuroscience.* 2001; 2:840-843.
43. Zhang P, Li J, Liu Y et al. Human neural stem cell transplantation attenuates apoptosis and improves neurological functions after cerebral ischemia in rats. *Acta anaesthesiologica Scandinavica.* 2009; 53:1184-1191.
44. Chen B, Gao X Q, Yang C X et al. Neuroprotective effect of grafting GDNF gene-modified neural stem cells on cerebral ischemia in rats. *Brain research.* 2009; 1284:1-11.
45. Bliss T, Guzman R, Daadi M et al. Cell transplantation therapy for stroke. *Stroke; a journal of cerebral circulation.* 2007; 38:817-826.
46. Hosper N A, Bank R A, van den Berg P P. Human amniotic fluid-derived mesenchymal cells from fetuses with a neural tube defect do not deposit collagen type i protein after TGF-beta1 stimulation in vitro. *Stem cells and development.* 2014; 23:555-562

---

What is claimed is:

1. A method for obtaining isolated human neural stem cells, consisting of:
   (a) collecting cells from amniotic fluid obtained from a pregnant human subject whose fetus has been diagnosed to have a neural tube defect;
   (b) incubating the cells with a culture medium;
   (c) detecting expression levels of Nestin, Sox2, Musashi-1, and ATP-binding cassette G2 (ABCG2) markers and activity of Stage-Specific Embryonic Antigen-3 (SSEA-3), Stage-Specific Embryonic Antigen-4 (SSEA-4), Tumor Rejection Antigen-1-60 (TRA-1-60), Tumor Rejection Antigen-1-81 (TRA-1-81) and telomerase in the cells; and
   (d) isolating from the culture medium human neural stem cells that express Nestin, Sox2, Musashi-1 and ABCG2 markers and exhibit telomerase activity but do not express SSEA-3, SSEA-4, TRA-1-60 and TRA-1-81.

2. The method of claim 1, wherein the neural tube defect is anencephaly or myelomeningocele.

3. The method of claim 2, wherein the neural tube defect is anencephaly.

4. The method of claim 1, wherein the culture medium is a serum-free cell culture medium that allows the neural stem cells to proliferate.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccctgaccac tccagtttag                                                 20

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
cctctatggc tgtttctttc tc                                              22

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
ccggcacggc cattaac                                                    17

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
```

```
ctcccatttc cctcgttttt c                                              21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tgcaggcccg aaagagaaag                                                20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gatctgctgc agtgtgggtt t                                              21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tgcctcacac ggagactgtc t                                              21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
agtgggttgt ttgcctttgg                                                20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agctatgccc ggacctccat                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcctgcagca ggaggatctt                                                20

<210> SEQ ID NO 11
<211> LENGTH: 21
<212> TYPE: DNA
```

<213> ORGANISM: Artificial Sequence
<220> FEATURE:
<223> OTHER INFORMATION: Primer

<400> SEQUENCE: 11
aagccagcag tgtctaaacc c                                          21

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gggaggacga ggccataaat ac                                         22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gtgacaagga gtttcaaaca ggaa                                       24

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctgatggata actctgtgcg aga                                        23

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gcgaggagaa ccggatcac                                             19

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
ttcaccacga tgttcctctt ga                                         22

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cccagggaga agatggactt g                                          21

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ctttaacaca tcttgttgag cgtactc                        27

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
aggcagagcg tccgactata aa                             22

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
gactatctct tcctcccagc ttaaaa                         26

<210> SEQ ID NO 21
<211> LENGTH: 17
<212> TYPE: DNA
<213> ORGANISM: Artificial Sequence
<220> FEATURE:
<223> OTHER INFORMATION: Primer

<400> SEQUENCE: 21
cggcgttcgg tatcaga                                   17

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gaacggccac agttctaaga g                              21

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ggaccacaac atgctgctc                                 19

<210> SEQ ID NO 24
<211> LENGTH: 20
<212> TYPE: DNA
<213> ORGANISM: Artificial Sequence
<220> FEATURE:

<223> OTHER INFORMATION: Primer

<400> SEQUENCE: 24
cactccattc agaaggtgcc                                              20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ccgaaaggtc cgagagacac t                                            21

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
agcttcttca tctttgctct ttgg                                         24

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
cctgacccct gggcttgat                                               19

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
gtatgtctgt gtgcctgaca cgtt                                         24

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
ggcgaaccct gactatcaaa tg                                           22

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
gccccggatg atctccat                                                18

```
<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
tgtggatcag caagcaggag ta                                              22

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
caagaaaggg tgtaacgcaa ctaag                                           25
```